US007368295B2

(12) United States Patent
Tovar et al.

(10) Patent No.: US 7,368,295 B2
(45) Date of Patent: May 6, 2008

(54) NANOPARTICLES COMPRISING BIOLOGICALLY ACTIVE TNF WHICH IS IMMOBILIZED ON THE SAME

(75) Inventors: Günter Tovar, Stuttgart (DE); Thomas Schiestel, Stuttgart (DE); Herwig Brunner, Stuttgart (DE); Klaus Pfizenmaier, Tiefenbronn (DE); Matthias Grell, Darmstadt (DE); Peter Scheurich, Stuttgart (DE); Angela Hammer, Stuttgart (DE)

(73) Assignee: Fraunhofer-Gesellschaft zur Foderung der Angewandten Forschung E.V. (DE)

( * ) Notice: Subject to any disclaimer, the term of this patent is extended or adjusted under 35 U.S.C. 154(b) by 540 days.

(21) Appl. No.: 10/488,374

(22) PCT Filed: Aug. 16, 2002

(86) PCT No.: PCT/EP02/09185

§ 371 (c)(1),
(2), (4) Date: May 21, 2004

(87) PCT Pub. No.: WO03/020320

PCT Pub. Date: Mar. 13, 2003

(65) Prior Publication Data

US 2004/0265392 A1   Dec. 30, 2004

(30) Foreign Application Priority Data

Aug. 31, 2001   (DE) ................ 101 44 252

(51) Int. Cl.
   *G01N 33/553*   (2006.01)
(52) U.S. Cl. ...................... 436/526; 436/518
(58) Field of Classification Search ................ 436/526, 436/518; 435/7.1, 7.92, 287.1
   See application file for complete search history.

(56) References Cited

U.S. PATENT DOCUMENTS

| 6,274,552 B1 | 8/2001 | Tamarkin et al. ............. 514/12 |
| 2003/0082595 A1* | 5/2003 | Jiang et al. ................... 435/6 |

FOREIGN PATENT DOCUMENTS

| DE | 100 45 592 | 3/2002 |
| DE | 100 45 592 A1 | 3/2002 |
| EP | 0 247 860 A2 | 12/1987 |
| WO | WO 90/09798 | 9/1990 |
| WO | WO 93/12142 | 6/1993 |
| WO | WO 99/62535 | 12/1999 |

OTHER PUBLICATIONS

Fassina et al., "Binding of Human Tumor Necrosis Factor alpha to Multimeric Complementary Peptides", Archives of Biochemistry and Biophysics, vol. 296, No. 1, July, pp. 137-143, 1992.*

International Search Report dated Mar. 10, 2003 issued in relation to PCT application No. PCT/EP 02/09185.
"Antitumor Activity of Tumor Necrosis Factor-α Conjugated with Polyvinylpyrrolidone on Solid Tumors in Mice", Haruhiko Kamada, et al., *Cancer Research* 60, 6416-6420, Nov. 15, 2000, XP-002231438.
"Treatment with Liposome-Bound Recombinant Human Tumor Necrosis Factor-α Supresses Parasitemia and Protects against *Plasmodium berghei* k173-Induced Experimental Cerebral Malaria in Mice", N.S. Postma, et al., *The Journal of Pharmacology and Experimental Therepeutics*, JPET 288:114-120, 1999, XP-002231657.
Preparation and Characterization of Liposomal-Lipophilic Tumor Necrosis Factor, Toshihiko Utsumi, et al., *Cancer Research* 51, 3362-3366, Jul. 1, 1991, XP-001145748.
"Binding of Human Tumor Necrosis Factor α to Multimeric Complementary Peptides", Giorgio Fassina, et al., *Archives of Biochemistry and Biophysics*, vol. 296, No. 1, July, pp. 137-143, 1992; XP-09003847.
"Enhanced Antitumor Potency of Polyethylene Glycolyated Tumor Necrosis Factor-α: A Novel Polymer-Conjugation Technique with a reversible Amino-Protective Reagent",Shinichi Tsunoda, et al., *The Journal of Pharmacology and Experimental Therepeutics*, JPET 290:368-372, 1999, XP-002231935.
"Cytotoxic and Antitumor Activity of a Recombinant Tumor Necrosis Factor-B1(Fv) Fusion Protein on Le$^y$ Antigen-expressing Human Cancer Cells", Uwe Scherf, et al., *Clinical Cancer Research*, vol. 2, 1523-1531, Sep. 1996, XP-000653372.
"A Genetically Modified Recombinant Tumor Necrosis Factor-α Conjugated to the Distal Terminals of Liposomal Surface Grafted Polyethyleneglycol Chains", Michalakis Savva, et al., *International Journal of Pharmaceutics*, 184 (1999) 45-51, XP-001121142.
"Suppression of Syndecan-1 Expression in Endothelial Cells by Tumor Necrosis Factor-α", Varpu Kainulainen, et al., *The Journal of Biological Chemistry*, vol. 271, No. 31, pp. 18759-18766, Aug. 2, 1996, XP-002231936.
"Gelatin Beads as Platforms for Targeting Molecule and Anti-Fas Antibody: Two Major Properties of Cytotoxic T Lymphocytes", Toshiya Yokozawa, et al., *Experimental Hematology*, 28 (2000) 1129-1136.

(Continued)

*Primary Examiner*—Ann Y. Lam
(74) *Attorney, Agent, or Firm*—Ostrolenk, Faber, Gerb & Soffen, LLP

(57) ABSTRACT

The present invention relates to nanoparticles with tumor necrosis factor (TNF) or cytokine immobilized thereon, where TNF or the cytokine is preferably immobilized in the form of a trimer in directed fashion and with retention of its biological activity on the carrier, to methods for the directed immobilization of TNF or cytokine on nanoparticles, to the use of the nanoparticles having immobilized TNF or cytokine for the identification and/or isolation of cytokine- or TNF-binding partners and for the identification and/or isolation of inhibitors of the interaction between TNF or cytokine and its binding partners, to the use of such nanoparticles for preparing a pharmaceutical composition, in particular for the therapy of tumors, and to pharmaceutical and diagnostic compositions which comprise such nanoparticles.

67 Claims, 12 Drawing Sheets

OTHER PUBLICATIONS

"Analysis for TNF-α Using Solid-Phase Affinity Capture with Radiolabel and MALDI-MS Detection". Gregory B. Hurst, et al., *Analytical Chemistry*, vol. 71, No. 20, Oct. 15, 1999, 4727-4733.

"Suppression of Syndecan-1 Expression in Endothelial Cells by Tumor Necrosis Factor-α", Varpu Kainulainen, et al., *The Journal of Biological Chemistry*, vol. 271, No. 31, pp. 18759-18766, Aug. 2, 1996.

"In Vitro and In Vivo Release Properties of Brilliant Blue and Tumour Necrosis Factor-Alpha (TNF-α) From Poly (D,L-lactic-co-glycolic acid) Multiphase Microspheres", M. Iwata, et al., *Journal of Microencapsulation*, 1999, vol. 16, No. 6, 777-792.

"Ability of Cell-Sized Beads Bearing Tumor Cell Membrane Proteins to Stimulate LAK cells to Secrete Interferon-γ and Tumor Necrosis Factor-α", Anita S.-F. Chong, et al., *Cellular Immunology*, 134, 96-110 (1991).

"Kinetic Analysis of TNF-α Oligomer-Monomer Transition by Surface Plasmon Resonance and Immunochemical Methods", Claudio Poiesi, et al., *Cytokine*, vol. 5, No. 6 (Nov. 1993), pp. 539-545.

"Binding of Human Tumor Necrosis Factor α to Multimeric Complementary Peptides", Giorgio Fassina, *Archives of Biochemistry and Biophysics*, vol. 296, No. 1, July, pp. 137-143, 1992.

"Antitumor Activity of Tumor Necrosis Factorα Conjugated with Polyvinylpyrrolidone on Solid Tumors in Mice", Haruhiko Kamada, et al., *Cancer Research* 60, 6416-6420, Nov. 15, 2000.

Postma et al., Treatment with Liposome-Bound Recombinant Human Tumor Necrosis Factor-α Suppresses Parasitemia and Protects against *Plasmodium berghei* k173-Induced Experimental Cerebral Malaria in Mice, The Journal of Pharmacology and Experimental Therapeutics, vol. 288, No. 1, 114-120, 1999.

Tsutomu Arakawa et al., Molecular Weight of Recombinant Human Tumor Necrosis Factor-α, The Journal of Biological Chemistry, vol. 262 No. 16, pp. 7484-7485, Jun. 5, 1987.

Paul Wingfield, et al., Tumour necrosis factor is a compact trimer, FEBS Letters, vol. 211, No. 2, 179-184, Jan. 1987.

Search report dated Mar. 22, 2007.

* cited by examiner

Figure 1: Bioassay (KYM-1 target cell)

Figure 3: Bioassay (target cell: KYM-1)

Figure 4: Bioassay (target cell: KYM-1)

Figure 5: Bioassay (target cell: Colo205)

Figure 6: Bioassay (target cell: KYM-1)

Figure 7: Bioassay (target cell: mouse fibroblasts)

Figure 8
Cys TNF on TNF R1 Fc
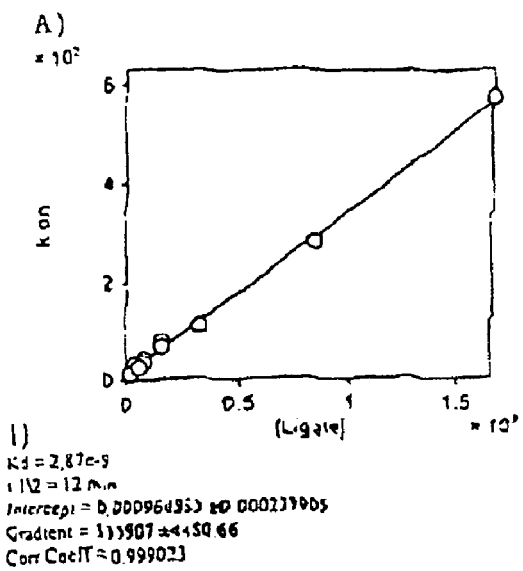
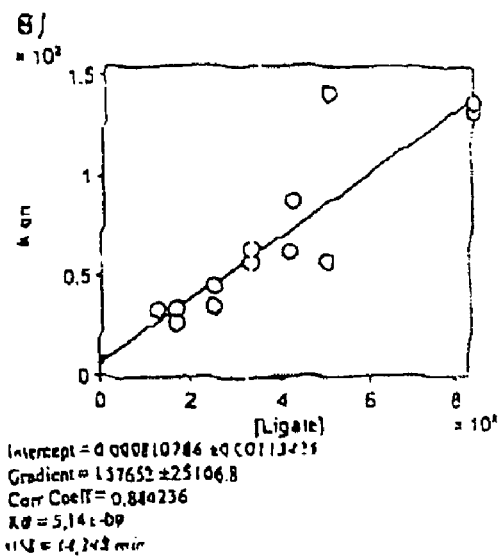
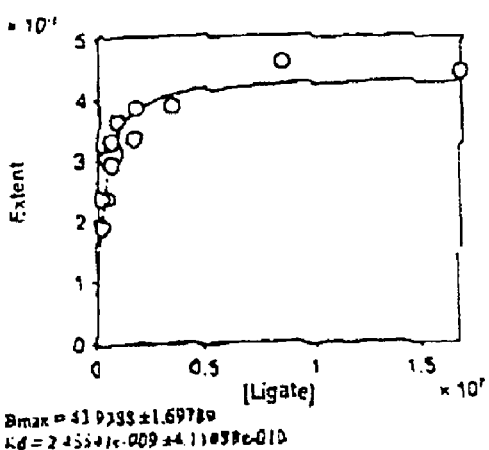
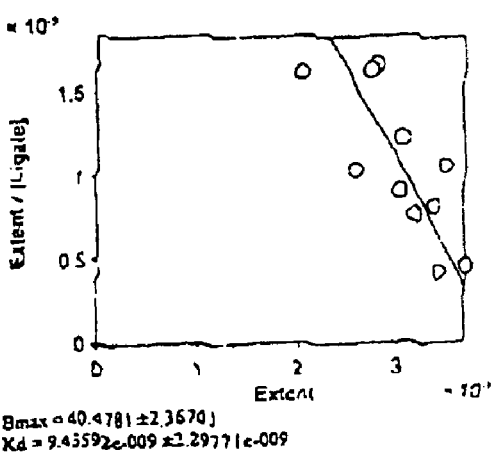
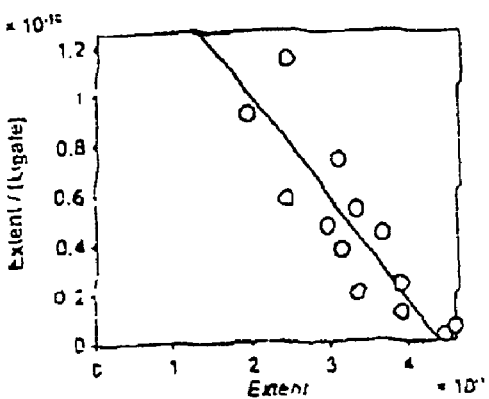
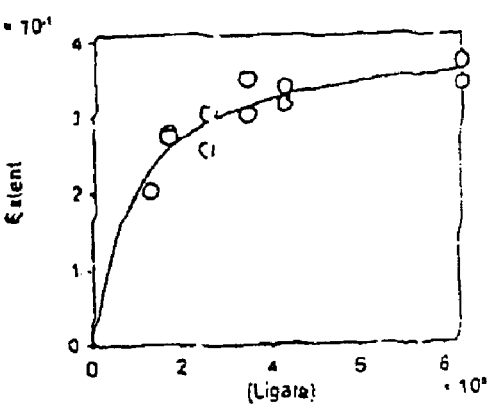

Figure 9
Cys TNF on TNF R2 Fc
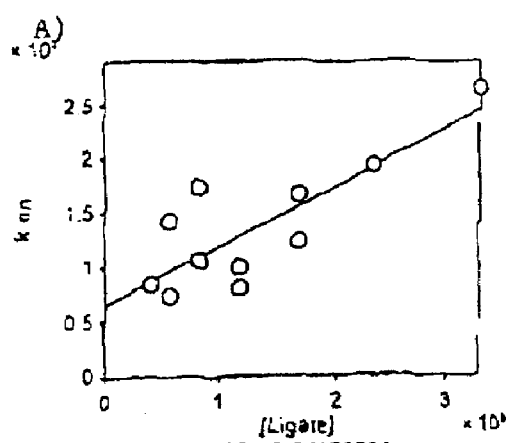
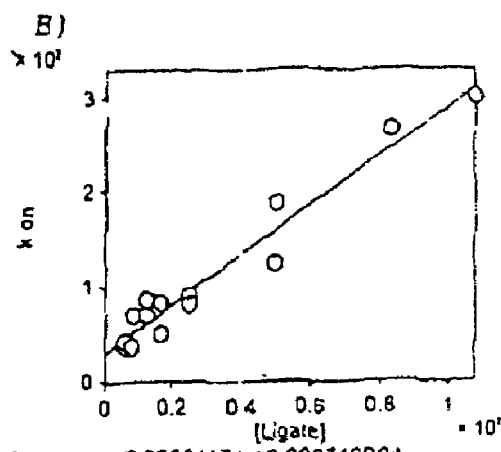
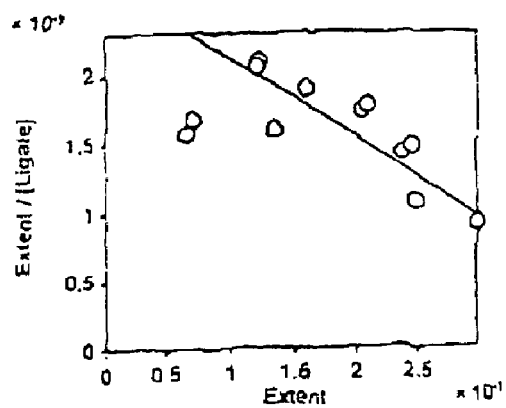
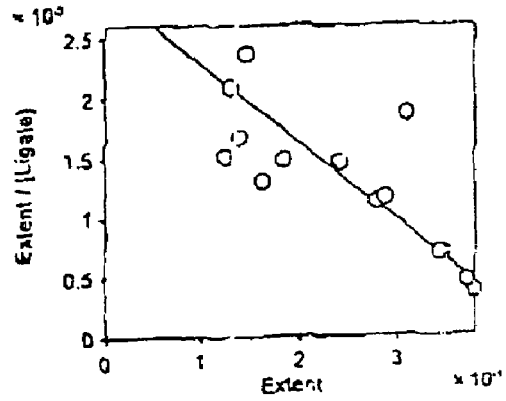
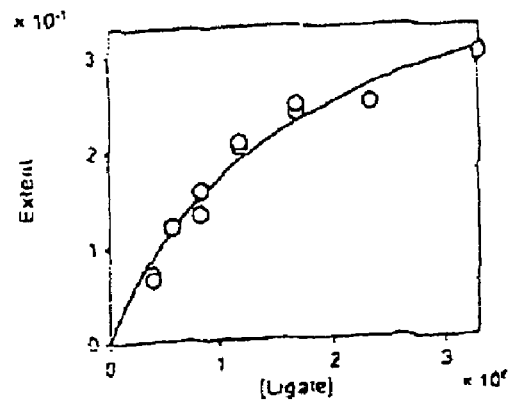
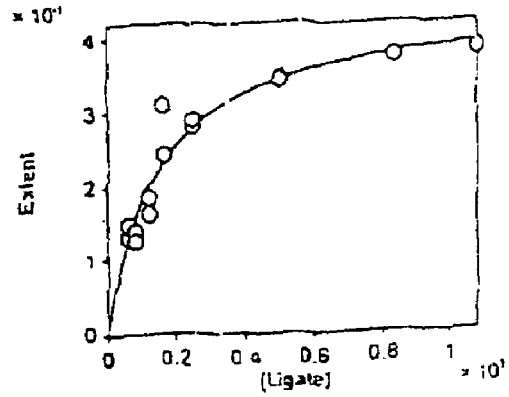

Figure 10
TNF on TNF R1 Fc
A)
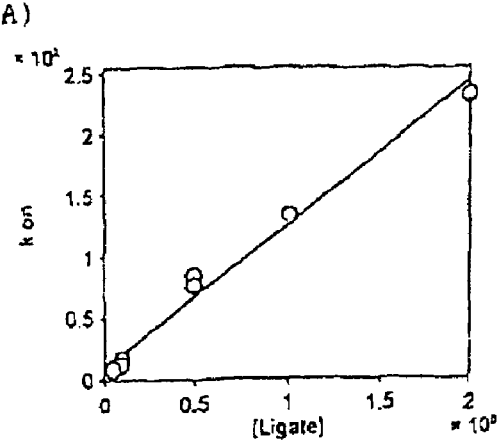
Kd = 6.835e-10
t1\2 = 14.3
Intercept = 0.000808166 ±0.000420326
Gradient = 1.18243e+006 ±52025.1
Corr Coeff = 0.992345
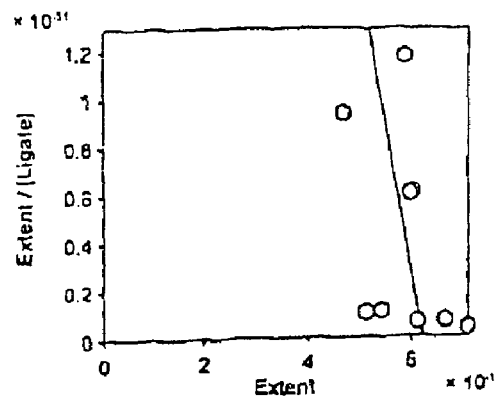
Bmax = 62.2475 ±3.35551
Kd = 8.45696e-011 ±6.33615e-011
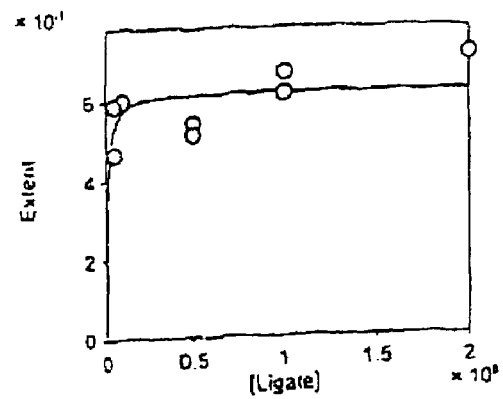
alte Küvette [3 Monate]
B)
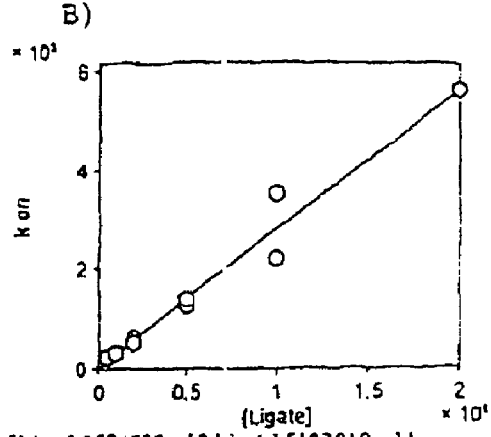
Kd = 5.7574739e-10 bis 4.15123019e-11
t1\2 = 7.1574 min bis 99.26 min
Intercept = 0.000116376 ±0.00149768
Gradient = 2.80341e+006 ±184316
CorrCoeff=0.983145
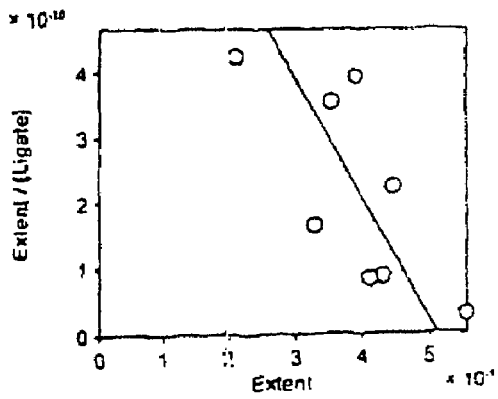
Bmax = 51.1614 ±4.27426
Kd = 5.43365e-010 ±2.04602e-010
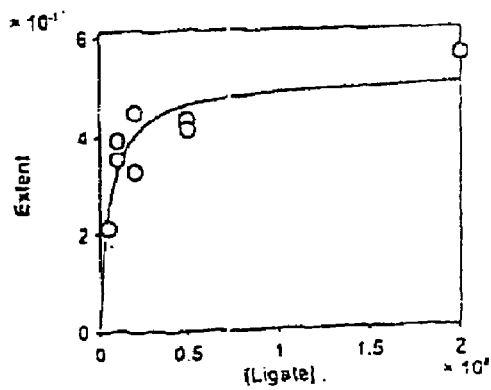
besoffene Werte Figure 11
TNF on TNF R2 Fc
A)
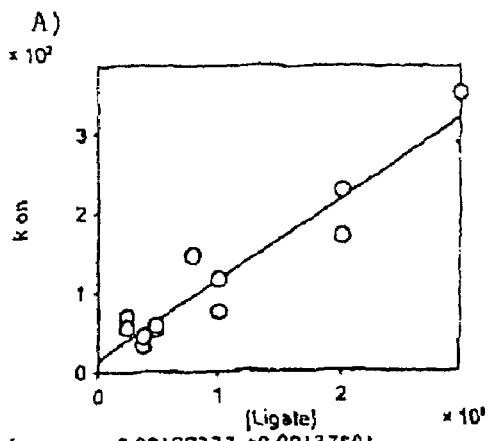
Intercept = 0.00127333 ±0.00137801
Gradient = 1.02935e+006 ±105212
Corr Coeff = 0.95153
Kd = 1.237e-9
t 1\2 = 9.073
B)
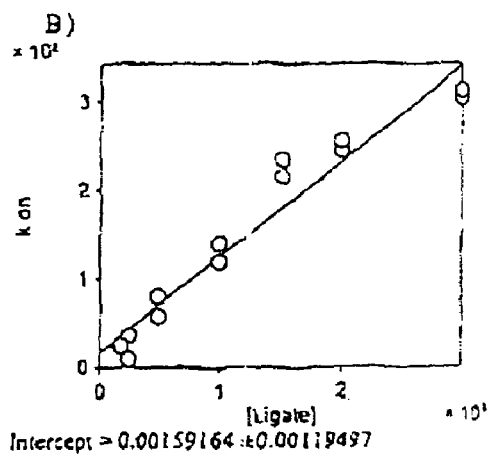
Intercept = 0.00159164 ±0.00119497
Gradient = 1.08249e+006 ±77610.4
Corr Coeff = 0.970515
Kd = 1.47e-9
t 1\2 = 7.25
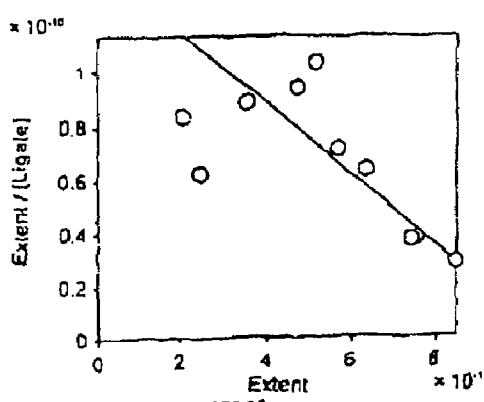
Bmax = 106.601 ±8.57988
Kd = 7.56256e-009 ±1.48899e-009
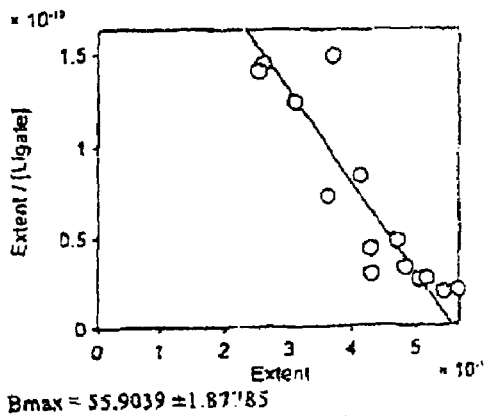
Bmax = 55.9039 ±1.87185
Kd = 1.99244e-009 ±3.33318e-010
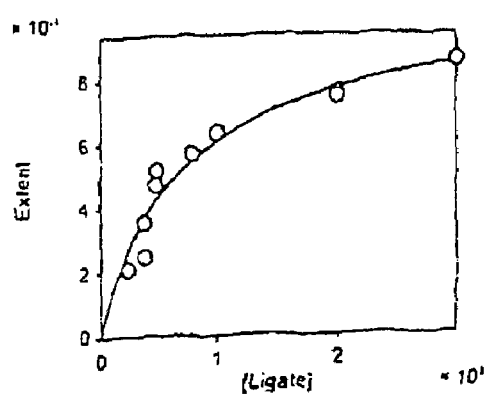
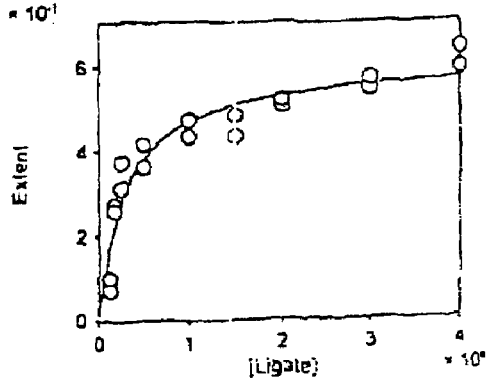

Concentration of modifier

NANOPARTICLES COMPRISING BIOLOGICALLY ACTIVE TNF WHICH IS IMMOBILIZED ON THE SAME

The present invention relates to nanoparticles with tumor necrosis factor (TNF) immobilized thereon, with TNF being immobilized in the form of a trimer in directed fashion and with retention of its biological activity on the carrier, to methods for the directed immobilization of TNF on nanoparticles, to the use of nanoparticles having immobilized TNF for the identification and/or isolation of TNF binding partners and for the identification and/or isolation of inhibitors of the interaction between TNF and its binding partners, to the use of such nanoparticles for preparing a pharmaceutical composition and in particular for the therapy of tumors, and to pharmaceutical and diagnostic compositions which comprise such nanoparticles.

In living biological tissues, a coordinated signal transmission between different cells and/or cell compartments, i.e. across membrane structures, is necessary in order to maintain homeostasis and make adaptation to external changes possible. As the inter- and intracellular signal transduction mechanisms mediated by soluble mediators are by now well characterized on the basis of numerous examples, intercellular signals mediated by membrane-associated interaction partners are often still not understood to a large extent. Cell-mediated signals are, however, essential for all multicellular organisms and thus also for maintaining multicellular organ assemblages in higher life forms. Thus, it has emerged that when normal body cells are removed from their tissue assemblage they lose important survival signals. They then die by a process which is referred to as anoikis (isolation), the molecular mechanism of which corresponds to programmed cell death (apoptosis). Knowledge about such survival signals and their molecular mechanisms of action is particularly relevant to the whole area of oncology because tumor cells must bypass or switch off exactly these regulatory systems in order to be able to form malignant tumors.

The problems associated with research into intercellular signal mechanisms are in part purely technical. Thus, for example, in many cases it is impossible or very complicated for methodological or technical reasons to allow two different cell populations to interact in a spatially and temporally controlled manner and to observe their reactions in parallel during this. In addition, such an interaction always triggers a large number of signals which it is scarcely possible, or impossible, to assign to the large number of signal molecules. In order to be able to determine specifically the effect of an individual signaling substance, therefore, in the state of the art there is preparation and investigation of recombinant soluble derivatives of membrane-associated ligands and their receptors. The data obtained in this way may, however, lead to an incorrect estimation of the actual physiological significance of a defined signaling process, because the underlying test system represents a gross simplification in relation to the actual event.

Tumor necrosis factor belongs to the class of cytokines, which are substances which are produced and secreted by a large number of cell types and which regulate, as intercellular mediators, a large number of cellular processes. Cytokines include, for example, lymphokines, interleukins, monokines and growth factors. Tumor necrosis factor (TNF, also called TNF-α or cachectin) is the eponymous member of a large gene family of cytokines which are structurally homologous and have diverse biological properties, some of which overlap. The members known at present include TNF itself and, inter alia, lymphotoxin alpha (LT-α) which, like TNF, binds to the same receptors (TNFR1 and TNFR2) and displays very similar signaling properties, and LT-β, FasL, CD27L, CD30L, CD40L, TWEAK, OX40L, EDA, AITRL, VEGI, LIGHT, 4-1BBL, APRIL, BLYS, RANKL and TRAIL, for each of which one or more specific membrane receptors exist (Locksley et al., Cell, 104:487-501, 2001). The molecules of the tumor necrosis factor (TNF) ligand family are involved via their complementary receptors, which are collected into the TNF receptor family, in a large number of in particular immunoregulatory processes. Apart from very few exceptions, the members of the TNF ligand family are membrane proteins of type II (Locksley et al., see above). However, it is also possible in many cases to derive soluble forms from these membrane-associated forms by specific proteolysis or alternative splicing. In some cases insoluble and membrane-associated forms of members of the TNF ligand family may differ considerably in their bioactivity (Grell et al., Cell, 1995). In contrast to lymphotoxin (LT-α), which is a genuine secreted protein, however, TNF is, like most other members of the TNF family, produced by the producing cell always initially as membrane-associated TNF from which the classical soluble cytokine TNF is formed only on proteolytic cleavage. This membrane TNF is a genuine transmembrane protein which exists in trimeric form and is biologically active. It has been possible to show in this connection that membrane TNF has a special range of cellular effects which are not attained by soluble TNF and by LT-α either (Grell et al., Cell, 83 (1995), 793-802). It is of interest that other members of the TNF family behave similarly, i.e. they are bioactive in the normal, membrane-associated form, and, as molecules which are soluble after proteolytic processing or occur in soluble form otherwise, either entirely biologically inactive or show, as in the case of TNF, a restricted range of effects. Apart from TNF, this has been shown for example also for FasL, TRAIL and CD40L (Wajant and Pfizenmaier, Onkologie, 24:6-10, 2001). TNF is formed primarily by macrophages/monocytes, lymphocytes and mast cells and influences inflammations, sepsis, lipid and protein metabolism, blood formation, angiogenesis, wound healing and immune defenses and exerts cytotoxic or cytostatic effects on certain tumor cells. Lymphotoxin α likewise has cytotoxic effects on certain tumor cell lines. Relatively little is known about the molecular basis of the diverse effects of TNF-α in vivo and in vitro. Analysis of the crystal structure of the recombinant soluble TNF-α molecule has revealed that this substance is an oligomeric protein consisting of three identical subunits each of 17.5 kDA.

To date, two different TNF-specific membrane receptors of 55 kDA (TNFR1) and 75 kDA (TNFR2) have been identified. It is known that TNF-α oligomers must bind to the membrane receptors for it to be possible to induce at least in physiological solutions some of the various biological activities of TNF-α. Although it has been shown that TNF-α occurs as oligomer in solution, it has emerged, however, that these non-covalently linked TNF-α oligomers are unstable and are converted into inactive forms. It is, however, assumed that the structural changes of TNF-α also take place in vivo because monomers and oligomers are found in different proportions in the cerebrospinal fluid of patients with meningitis.

TNF-α was originally identified as an endotoxin-induced factor able to induce the necrosis of tumors in mice. However, it is known that the antitumor effect of TNF-α not only results from the cytoxic effects on tumor cells but is also based on activation of antitumor effector immune cells in the blood, for example macrophages, cytotoxic lymphocytes and neutrophils. The antitumor effect of TNF-α is additionally based on a specific damage to tumor blood vessels.

Since TNF-α has very low stability and exerts pleiotropic effects in vivo, attempts to date to employ TNF-α as systemic antitumor agent have been unsuccessful. It has emerged on administration of TNF-α that extremely severe systemic side effects, such as fever and low blood pressure, occur before therapeutically effective doses are reached. Despite the continuing substantial expectations from potential use of TNF-α as antitumor agent, the clinical utilizability of this substance therefore continues to be very restricted.

It is generally difficult to employ biologically active proteins such as cytokines for therapeutic purposes because biologically active proteins very often display low stability and short half-lives. The proteins are rapidly removed from the blood by the liver, kidneys and other organs, with the rate of clearance depending on the size of the molecules and the extent of proteolysis. Plasma proteases in particular cause the degradation of such proteins and bring about rapid loss of the biological activity.

In order to overcome these problems, in recent years systems for immobilizing biological active proteins on or in carrier systems have been developed. For example, controlled release systems for therapeutic active ingredients or drugs are known, with drugs for example being immobilized by inclusion in a matrix. After administration of such controlled release systems there is then controlled release of the drugs through degradation processes within the living body. The conformation of the active ingredient in the immobilized state is not crucial in these systems. On the contrary, the important point is that the active ingredient is in the active state after release.

The immobilization of proteins on particulate systems is also known (Cell Separation and Protein Purification, Technical Handbook, $2^{nd}$ edition (1996), Dynal, Oslo), although the protein binding to the particles takes place nonselectively, for example by means of adsorption, and not in a directed manner (Michaelis et al., Anticancer Drugs, 11 (5) (2000), 369-376). In addition, simple transfer of the findings obtained in this connection to immobilization on nanoparticles is not directly possible, because varying the functional surface groups is always associated with an intervention in the colloidal system and may, for example, induce unwanted coagulation.

Yokozawa et al., Exp. Hematol., 28 (10) (2000), 1129-1136, describe the non-covalent immobilization of Fas-specific antibodies on gelatin beads 2.5 µm in size. The antibodies are in this case immobilized by adsorption, that is to say not in a directed manner. These systems, which are called artificial cells, are able to induce apoptosis on target cells.

Hurst et al., Anal. Chem., 71 (1999), 4727-4733, describe the covalent surface modification of magnetic polymer particles with a size in the µm range with TNF antibodies, with which TNF can subsequently be captured from a complex solution. This method is used for sample preparation for MALDI-TOF-MS methods. Immobilization of a protein via an antibody is admittedly in principle a directed immobilization. However, such a protein immobilization is very unstable compared with a covalent bond.

The immobilization of TNF on agarose particles or in PLGA particles is also known (Kanulainen et al., J. Biol. Chem., 273/31 (1996), 18759-18766; Iwata et al., J. Microencaps., 16 (1999), 777-792). There is no covalent attachment of TNF in these cases either. TNF is subsequently released slowly by the particles and is biologically active only in dissolved form.

Chong et al., Cell. Immunol., 134 (1) (1991), 96-110, describe the immobilization of tumor membrane proteins on hydrophobic particles. These systems, called pseudocytes, are used to stimulate on other cells the production of cytokines, for example TNF, and thus to induce the lysis of tumor cells. This is therefore an indirect approach.

Poiesi et al., Cytokine, 5/6 (1993), 539-545, describe the immobilization of TNF on planar chip surfaces for surface plasmon resonance investigations. Standard protein chemical methods such as EDC and NHS were employed for the immobilization. It emerged from this that the molecule was not stably bound because some of the TNF could be removed by washing.

Fassina et al., Arch. Biochem. Biophys., 296 (1992), 137-143, describe the preparation of multimeric complementary peptides for TNF. These were subsequently immobilized on chromatography columns and microtiter plates. These substances were then used to remove TNF trimers from complex matrices. However, the interaction between peptide and TNF is too small for permanent immobilization of TNF.

Kamada et al., Cancer Res., 60 (2000), 6416-6420, describe the covalent conjugation of TNF with polymers such as PVD or PEG in order to increase the biological activity and the bioavailability. For this purpose, short-chain polymers are covalently bonded to amino groups of TNF, as it were individual TNF molecules coated with polymer. The immobilization of the polymers on the TNF achieves no crosslinking or anything like it, and the TNF trimers are thus not stabilized either. On the contrary, the bioactivity of TNF decreases greatly with the degree of coating. The intention of this approach is to improve the bioavailability of the dissolved form of TNF. In contrast to the present invention, it is not possible thereby to attain the mode of action of the membrane-associated form.

The present invention is therefore based on the technical problem of providing means and methods for the immobilization of tumor necrosis factor (TNF) or of another member of the TNF family on a carrier surface, with TNF being immobilized in such a way that its biological activities present before the immobilization are also retained in the immobilized state, so that immobilized TNF is able for example to interact with its receptors and thus its biological activities can be induced. The immobilized TNF—or another molecule of the same family—is to display in particular the biological properties which are characteristic of the membrane-associated form of the TNF molecule—or of the membrane-associated form of another member of the TNF family. It is intended in this connection that TNF in the immobilized state, i.e. together with its carrier, can be employed both for in vitro investigations, for example concerning its interaction with other cellular constituents, and as drug for the treatment of diseases, especially of neoplastic diseases, without the side effects known in the prior art occurring. It is intended that, in the period of use, there is negligible degradation of the support systems or of immobilized TNF, or, in the case of in vivo use, the degradation is to take place only at a later time after immobilized TNF has displayed its biological activity.

The present invention solves the technical problem on which it is based through the provision of nanoparticles comprising a carrier with a surface having functional groups 1 A and with at least one monomer of a protein of the TNF family, this at least one monomer having complementary functional groups 2 A which bind functional groups 1 A and being connected via the functional groups 2 A to the functional groups 1 A of the carrier. The invention thus provides for an immobilization of the monomer on the surface taking place via a binding between first functional groups 1 A present on the carrier surface and functional groups 2 A which are present in the monomer of the protein of the TNF family and are complementary to the functional groups 1 A and are able to enter into an affinity binding, preferably covalent, with the latter. The functional group 2 A is preferably positioned within the monomer of the protein of the TNF family in such a way that it is disposed outside the domains responsible for the biological activity, at a suitable distance from these domains, and thus ensures retention of the biological activity of the monomers or of a monomer complex on the carrier. It is possible to provide according to the invention for only one monomer to be linked in the manner described to the carrier, and thus immobilized. However, in a preferred embodiment, it is also possible according to the invention to provide for a plurality of, in particular three, monomers each to be linked via their functional groups 2 A to the carrier, and in a particularly preferred embodiment to be immobilized in the form of a primer. In a further preferred embodiment, it is possible to provide for only a first monomer to be linked via its functional groups 2 A to the functional groups 1 A of the carrier, in which case, however, this first monomer is present associated, for example via a covalent or non-covalent binding, with at least one further, for example two further, monomer(s) in a biologically functional unit, for example in the form of a trimer. This one or more further monomers are, in a preferred embodiment, not linked directly, covalently or non-covalently, to the carrier but are immobilized solely through the interaction with the first monomer on the carrier. Immobilization of each of these monomers can thus take place on the one hand by this monomer entering directly into an affinity binding, preferably covalent, via its functional groups 2 A with the functional groups 1 A of the carrier. On the other hand, it is possible according to the invention for the immobilization also to be provided by one monomer being present associated via a non-covalent or covalent binding with another monomer which in turn is linked via its functional groups 2 A to the functional groups 1 A of the carrier, so that the associated monomer enters into absolutely no direct binding with the carrier. The invention also provides in a preferred embodiment for each monomer to have a binding both with the carrier and with a further monomer.

There are thus according to the invention various possibilities for immobilizing TNF as trimer. Each monomer unit has in a preferred embodiment a functional group which is suitable for a preferably covalent immobilization. Preference is given to each trimer being immobilized via three covalent bonds. It is, however, also possible for only one or two covalent bonds to be formed between TNF trimer and particle and for the trimer to be stabilized by disulfide bridges between the monomers and/or non-covalent interactions.

It is also possible according to the invention, for example in the case of LT-α and LT-β, for bioactive heteromers to form, e.g. LT-$α_1$LT-$β_2$ or LT-$α_2$LT-$β_1$, which in turn are also preferably immobilized via three or else via one or two covalent bonds.

The bioactivity of membrane-associated TNF is attained according to the invention inter alia by a plurality of TNF trimers being disposed adjacently on the cell surface. When the cell interacts with an adjacent cell, corresponding receptors are bound and undergo complementary arrangement on the neighboring cell. Only when this receptor cluster has formed is the appropriate signal response initiated. Exactly such clustering and the signal cascade linked thereto is initiated by the immobilization of the TNF on the particle surface, i.e. on the particles of the invention the TNF molecules are immobilized in a favorable geometric density on the particle surface. This density of the immobilized TNF is achieved inter alia by attaching the functional groups 1 A and 1 B, which are utilized for binding the TNF molecules, in an appropriate density (this is demonstrated for example by zeta potential measurements, compare FIG. 12).

It is possible in a preferred embodiment of the present invention in the case where more than one monomer is present immobilized on the carrier, these monomers are monomers which are identical to one another, i.e. are present immobilized as trimers formed from homomers. It is possible in a further embodiment to provide for a plurality of monomers differing in type to be present, i.e. in a particularly preferred embodiment for immobilized trimers formed from heteromers to be present.

In connection with the present invention, a "protein of the TNF family" (TNF: tumor necrosis factor) means the TNF molecule itself and all members of the proteins which belong to the TNF family and which exert specific activities in vivo and/or in vitro via appropriate receptors which are specific for the respective TNF family member, i.e. are complementary, in particular TNF-α, LT-α and LT-β, FasL, TRAIL, CD40L, CD27L, CD30L, OX40L, EDA, AITRL, VEGI, LIGHT, TWEAK, 4-1BBL, APRIL, BLYS and RANKL. The term "protein of the TNF family" is used hereinafter as having the same meaning as the abbreviation TNF and vice versa unless stated otherwise. Thus, according to the invention, TNF is a protein that has in vivo an influence on inflammations, sepsis, lipid and protein metabolism, blood formation, angiogenesis, wound healing and immune defenses and exerts in vitro and/or in vivo inter alia cytotoxic (apoptosis and necrosis) or cytostatic effects, but also influences cell proliferation and differentiation. TNF is moreover a protein which is at least transiently located on a cell surface within a natural cell assemblage and controls the communication of the cell with its surroundings. In particular, TNF can make contact with cells on whose surface the complementary receptors (for example TNFR1 and TNFR2 for TNF, TRAILR 1-4 for TRAIL) are present and initiate TNF-specific signals and thus TNF-specific effects.

The present invention solves the technical problem on which it is based in a preferred embodiment of the present invention through the provision of nanoparticles comprising a carrier with a surface having functional groups 1 A and with, immobilized on the carrier, TNF with complementary functional groups 2 A which bind the functional groups 1 A, where TNF is immobilized in the form of a trimer.

The present invention provides in a preferred embodiment nanoparticulate carrier systems, in particular nanoparticles, with TNF immobilized thereon, where the immobilization is based on an affinity binding of TNF to the nanoparticle surface. The immobilization of TNF on the nanoparticles takes place according to the invention via a binding between first functional groups 1 A present on the carrier surface, and functional groups 2 A which are present in the TNF molecule and which are complementary to the functional groups 1 A and are able to enter into an affinity bindings, preferably covalent, therewith. The functional group 2 A of TNF is preferably positioned within the TNF molecule in such a way that it is disposed outside the domains responsible for the biological TNF activity, at a suitable distance from these domains. Directed immobilization of TNF, with retention of its biological activities, on the carrier is possible in this way according to the invention.

After TNF immobilization, according to the invention TNF is fixed on the carrier surface in such a way that the three-dimensional structure of the domain(s) necessary for the biological activity is unchanged compared with non-immobilized TNF, and that the TNF domain(s) is/are freely accessible for cellular reaction partners on contact therewith. TNF is moreover fixed in the form of trimers. The invention provides for decomposition of TNF trimers being prevented by introducing particular protein elements, in particular those protein structures which naturally form firmly linked trimers. After such a stabilization, the invention then provides for not every TNF subunit of a TNF trimer necessarily being fixed via affinity bindings between the functional groups 1 A and 2 A on the surface of the nanoparticle carrier; on the contrary, it is sufficient if at least one TNF subunit of a trimer is bound on the carrier.

The invention provides in particular for the carrier systems used according to the invention to be compact or hollow nanoparticles with sizes between 5 and 500 nm. These consist either of organic or inorganic particle materials. The nature of the material can be varied according to the invention according to the later use, the carrier of the nanoparticles preferably consisting of biocompatible and/or biodegradable materials.

The nanoparticles of the invention on whose surface TNF is fixed therefore behave according to the invention in relation to the immobilized TNF molecules like cells. This means that the nanoparticles of the invention can for example make contact with cells on whose surface one or more TNF receptors, for example TNFR1 and TNFR2, are present and initiate TNF-specific signals and thus TNF-specific effects. Since the nanoparticles are smaller than 1 μm at least in one dimension, they are also referred to according to the invention as “nanocytes”.

Since the nanoparticles of the invention on the one hand react in analogy to membrane-associated molecules, but on the other hand also display completely novel surprising functions, the nanocytes of the invention have a very broad potential for use. The nanoparticles can be employed according to the invention as tools for molecular biology, cell biology and clinical research. In this connection, the use of the nanoparticles of the invention provides the advantage that established methods can be used for the bioactivity determination and thus material screening can be carried out quickly.

The nanoparticles of the invention can be employed for example in vitro in order to investigate the mode of action of membrane-associated molecules, in particular in signal transduction. Compared with direct cell-cell interaction, the nanoparticles of the invention provide the advantage that single effects can be investigated in isolation. The nanoparticles of the invention can therefore also be employed for in vitro diagnosis in order to identify and/or label for example particular cells, especially tumor cells. In addition, it is possible by using the nanoparticles of the invention deliberately to convert cells into a desired state, or there is a possibility of switching forward and backward between different cell states.

The nanoparticles of the invention can also be used to isolate particular cells from complex biological media or fluids such as blood, or to initiate appropriate reactions in these cells directly in these fluids or media, such as, for example, differentiation, proliferation or else apoptosis. It is additionally possible on the basis of the nanoparticles of the invention also to design technical systems which permit specific and continuous separation of particular cells.

The nanoparticles of the invention, especially those with biocompatible or biodegradable carrier systems, can be employed in vivo for the therapy of various diseases. Diseases which can in principle be treated using the nanoparticles of the invention are all those in which normal cell-cell interaction is impaired, i.e. in particular neoplastic diseases, wound healing processes and the like. Nanoparticles of the invention can, however, also be used for tasks which are normally undertaken by cells of the immune system. It is advantageously possible for the nanoparticles of the invention, in particular those based on biocompatible or biodegradable carrier systems, to be administered directly in vivo. The nanoparticles of the invention can also be deposited in the form of porous films. Microporous systems have a great potential for extracorporeal therapeutic applications, for example in the area of tumor therapy, for selective identification and, where appropriate, killing of freely circulating malignant cells.

A “protein” means in connection with the present invention a molecule which includes at least two amino acids connected together via an amide linkage. Thus, in connection with the present invention, a protein, especially TNF, may also be a peptide, for example an oligopeptide, a polypeptide or a part thereof, for example a domain or a binding cavity. The protein, in particular TNF, may be of natural or synthetic origin. It may be modified, compared with the wild-type protein, by methods of genetic manipulation and/or contain unnatural and/or unusual amino acids. A protein, in particular a TNF molecule, may be derivatized compared with the wild-type form, for example have glycosylations, it may be truncated, it may be fused to proteins or connected to molecules of another type, for example carbohydrates.

In connection with the present invention, “nanoparticles” mean binding matrices which comprise a carrier with a surface on which are disposed chemically reactive functional groups which are able to enter into affinity bindings, i.e. covalent and/or non-covalent bindings, with complementary functional groups of molecules to be bound, in particular TNF molecules, and in this way to fix the molecules stably on their surfaces. The carriers of the nanoparticles consist of chemically inert inorganic or organic materials and have a size of less than 1 μm, preferably of 5 to 500 nm.

In connection with the present invention, a “first functional group 1 A” means a chemical group which has been attached to the surface of the nanoparticle carrier and which is able to interact with a complementary functional group 2 A, which is present for example on the TNF molecule to be immobilized, in such a way that an affinity binding, preferably covalent, can take place between the two binding partners.

In a preferred embodiment of the invention, the first functional group 1 A of the carrier surface is selected from the group consisting of amino group, carboxy group, epoxy group, maleimido group, alkyl ketone group, aldehyde group, hydrazine group, hydrazide group, thiol group and thioester group.

The functional groups 2 A of the TNF molecules to be immobilized are selected according to the invention from a group which comprises the same species as for functional group 1 A of the carrier surface. A nanoparticle of the invention thus has in its surface a first functional group 1 A which is covalently linked to a functional group 2 A of the TNF molecule to be immobilized, the functional surface group 1 A being a group different from the functional protein group 2 A. The two groups 1 A and 2 A which bind together must in this case be complementary to one another, i.e. able to enter into a covalent bond with one another.

If an amino group is used according to the invention for example as functional group 1 A, the functional group 2 A of the protein to be immobilized is a carboxyl group. If conversely a carboxyl group is used according to the invention as functional surface group 1 A, the functional complementary protein group 2 A is according to the invention an amino group. If a thiol group is chosen according to the invention as functional surface group 1 A, the complementary protein group is according to the invention a maleimido group. If conversely a maleimido group is selected as functional surface group 1 A, the complementary functional protein group 2 A is according to the invention a thiol group. If an alkyl ketone group, in particular methyl ketone or aldehyde group, is used according to the invention as functional surface group 1 A, the functional complementary protein group 2 A is a hydrazine or hydrazide group. If conversely a hydrazine or hydrazide group is used according to the invention as functional surface group 1 A, the functional complementary protein group 2 A is according to the invention an alkyl ketone, in particular methyl ketone or aldehyde, group.

It is particularly preferred according to the invention for the functional group 1 A on the carrier surface of the nanoparticle to be a maleimido group and for the functional group 2 A of TNF to be a thiol group.

A preferred embodiment of the invention provides for directed immobilization of TNF as trimer with retention of its biological activity on the surface of the nanoparticles of the invention.

Immobilized TNF is according to the invention synthetic, naturally occurring or recombinantly prepared TNF with the wild-type sequence or with a mutated sequence. It is also possible according to the invention for TNF to be in chemically modified form.

In connection with the present invention, the term "immobilized in directed fashion" or "directed immobilization" means that a molecule, in particular TNF, is immobilized at defined positions within the TNF molecule on a carrier in such a way that the three-dimensional structure of the TNF domain(s) necessary for the biological activity is unchanged compared with the non-immobilized state and that this/these TNF domain(s), for example binding cavities for cellular reaction partners, is/are freely accessible for cellular reaction partners on contact therewith. "Immobilized in directed fashion" also means that the fixation of TNF on the carrier surface takes place in such a way that the immobilized protein can be degraded only very slowly, or not at all, by protein-degrading enzymes on later use in a cellular or cell-like environment. This means that the immobilized TNF molecule is aligned on the carrier surface in such a way that it provides as few points of attack for proteases as possible.

"Retention of the biological activity" means that TNF, especially the TNF trimer, is able to exert the same or virtually the same biological functions to at least a similar extent after immobilization on the surface of a nanoparticle as the same TNF molecules in the non-immobilized state under suitable in vitro conditions or the same TNF molecules in their natural cellular environment.

In connection with the present invention, a "trimer" or "TNF trimer" means a compound which is formed by linkage of three subunits, especially three TNF monomers, with the monomers being linked together preferably by the formation of disulfide bridges between cysteine residues. Trimerization of TNF leads to stabilization of the molecules compared with the TNF monomer. The three TNF subunits linked to give a trimer may be identical TNF monomers, i.e. the trimer may be in the form of a homotrimer. However, the trimer may according to the invention also include different TNF monomers, in which case the latter may differ both in respect of their composition, for example amino acid sequence, and in respect of their length. It is moreover unnecessary for each TNF subunit in the immobilized TNF trimer to be bound to the surface of the nanoparticle carrier. The TNF trimer may also be fixed onto nanoparticles by only one TNF subunit of the trimer being fixed via a covalent bond between its functional group 2 A and the functional group 1 A on the carrier.

The invention provides for the trimer formation to take place spontaneously either before or during the immobilization through high-affinity binding which is not covalent in nature, but also in particular by covalent formation of disulfide bridges between cysteine residues. A further preferred embodiment of the invention provides for the TNF molecules to be immobilized to contain a natural or synthetically prepared multimerization module which brings about the trimerization of TNF by high-affinity binding which is not covalent in nature, but in particular through the formation of covalent disulfide bridges, and thus a regular and stable trimerization of TNF. Particular preference is given according to the invention to introducing the tenascin C multimerization module, by genetic manipulation or by use of chemical synthetic methods, into the TNF molecules to be immobilized. The TNF molecules modified in this way are then trimerized either before or during the immobilization on the nanoparticles of the invention.

A further preferred embodiment of the invention provides for the surface of the nanoparticle of the invention to have further functional groups 1 B and TNF to have further complementary groups 2 B which bind the functional groups 1 B, where the functional groups 1 B and 2 B are able according to the invention to enter in particular into a non-covalent binding.

In connection with the present invention, a "second functional group 1 B" means a chemical group which is able to interact with any complementary functional group 2 B which is present in a TNF molecule to be immobilized, in such a way that a non-covalent binding between the two binding partners can take place.

In a preferred embodiment of the invention, the second functional group 1 B on the carrier surface is selected from the group consisting of oligohistidine group, Strep tag I, Strep tag II, desthiobiotin, biotin, chitin, chitin derivatives, chitin binding domain, metal ion chelate complex, streptavidin, streptactin, avidin and neutravidin.

The functional group 2 B of the TNF molecule to be immobilized is selected according to the invention from a group which comprises the same species as for functional group 1 B on the carrier surface. A nanoparticle of the invention thus has in its surface a functional group 1 B which is non-covalently linked to a functional group 2 B of TNF, the functional surface group 1 B being a group different from the functional TNF group 2 B. The two groups which enter into non-covalent binding with one another must be complementary to one another, i.e. be able to enter into a non-covalent binding with one another.

If a metal ion chelate complex is used according to the invention as functional surface group 1 B, the functional complementary TNF group 2 B is an oligohistidine group. If an oligohistidine group is used as functional surface group 1 B, the functional complementary TNF group 2 B is a metal chelate complex.

If Strep tag I, Strep tag II, biotin or desthiobiotin is used as functional surface group 1 B, streptavidin, streptactin, avidin or neutravidin is employed as complementary functional TNF group 2 B. If streptavidin, streptactin, avidin or neutravidin is employed as functional surface group 1 B, Strep tag I, Strep tag II, biotin or desthiobiotin is employed as complementary functional TNF group 2 B.

If in a further embodiment chitin or a chitin derivative is employed as functional surface group 1 B, a chitin binding domain is employed as functional complementary TNF group 2 B. If a chitin binding domain is employed as functional surface group 1 B, chitin or a chitin derivative is employed as functional complementary TNF group 2 B.

The aforementioned functional groups on the carrier surface and/or of TNF are preferably according to the invention connected by means of a spacer to the TNF molecule to be immobilized or to the carrier surface, or introduced onto the carrier or into the TNF molecule by use of a spacer. The spacer thus serves on the one hand to maintain the distance between the functional groups and the carrier or the TNF molecule, but on the other hand also as carrier for the functional group. Such a spacer can be according to the invention an alkylene or ethylene glycol spacer having 2 to 50 C atoms which, in a preferred embodiment, is substituted and has heteroatoms. The space may according to the invention be flexible and/or linear. When a spacer is used in connection with the first functional group 1 A on the surface, the spacer is covalently bonded to a side chain of an amino acid of TNF, it being possible for the amino acid to which the bonding takes place to be a natural or unnatural amino acid. Where the amino acid is a natural amino acid, it becomes an unnatural amino acid within the meaning of the invention through binding to the spacer and the functional first surface group 1 A connected thereto.

Where the spacer connects a functional TNF group 2 A to a carrier, this preferably takes place via a tethering group which is disposed on the carrier and which is preferably designed as silane with reactive groups, for example which is able to form covalent Si—O—Si linkages (silox attachments) with Si—OH groups on the surface of the preferably oxidic Si carriers.

For the purposes of the present invention, the spacer connects either a functional group of the carrier surface to TNF or a functional group of the protein to the carrier, it also being possible to regard the functional group as a constituent of the spacer, i.e. one of its functional groups.

In a particularly preferred embodiment of the invention, the amino group, carboxy group, epoxy group, maleimido group, alkyl ketone group, aldehyde group, hydrazine group, hydrazide group, thiol group or thioester group are used as first functional surface group 1 A, and are connected by means of a spacer, for example in the case of an alkyl ketone group by means of levulinic acid, to a side chain of a natural or unnatural amino acid present in the TNF molecule to be immobilized, or are introduced into the TNF molecule through the spacer. Where the connection takes place to a natural amino acid, the latter becomes an unnatural amino acid through the binding to the spacer having the functional group.

In connection with the present invention, a "carrier" means a chemically inert material which serves as support for the TNF molecule to be immobilized. In a preferred embodiment of the invention, the carrier consists of a biocompatible material. The carrier is according to the invention a compact or hollow particle having a size of from 5 nm to 500 nm. In connection with the present invention, the term "biocompatible" means that the carrier or the surface of the nanoparticle both in relation to its material composition and in relation to its structure elicits no immunological, toxic or other reaction either in the body of a recipient or in isolated biological tissues or fluids, and interferes with cellular or molecular processes scarcely or not at all. If a biocompatible carrier is "biodegradable" this means that a carrier can be slowly degraded or metabolized in the body of a recipient or in biological tissues or fluids, preferably after the TNF molecule immobilized on the carrier has displayed its biological activity, with the degradation or metabolic products not eliciting any immunological, toxic or other reactions and, moreover, being readily absorbed in the recipient's body.

A preferred embodiment of the invention provides for the carrier of the nanoparticle of the invention to comprise or to consist of a biocompatible, preferably an inorganic or an organic, material. In a preferred embodiment of the present invention, the nanoparticle of the invention consists of an inorganic carrier material such as silicon, $SiO_2$, SiO, a silicate, $Al_2O_3$, $SiO_2.Al_2O_3$, $ZrO_2$, $Fe_2O_3$, $Ag_2O$, $Zr_2O_3$, $Ta_2O_5$, zeolite, $TiO_2$, glass, indium tin oxide, hydroxyapatite, calcium phosphate, calcium carbonate, Au, $Fe_3O_4$, ZnS, CdSe or a mixture thereof. An organic biocompatible carrier material may be materials such as polypropylene, polystyrene, polyacrylates or a mixture thereof.

In a particularly preferred embodiment, the carrier of the nanoparticle of the invention consists of or comprises a biodegradable material. The biodegradable materials must be stable for the period of use, but may thereafter be degraded to result in excretable fragments. These are in particular polyesters of polylactic acid which have been additionally stabilized by crosslinking and thus in particular are biodegradable in a controlled fashion. It is particularly preferred to use a polyester of polylactic acid, especially poly(D,L-lactic acid-co-glycolic acid) (PLGA).

The carriers of the nanoparticles of the invention can be prepared using conventional methods known in the art, such as sol-gel synthetic methods, emulsion polymerization, suspension polymerization.

The surfaces of the nanoparticle carrier are designed to have specific functional groups through chemical modification reactions. These functional groups moreover have a chemical reactivity which is suitable for reaction with specific functional groups introduced into TNF molecules. The binding of TNF in this case takes place both covalently and non-covalently via a chemical reaction between TNF and surface. The carriers, especially the surfaces thereof, are therefore provided with suitable functional groups 1 A or functional groups 1 A and 1 B after the preparation thereof using conventional methods, for example graft polymerization, silanization, chemical derivatization etc. The density of the functional groups and the distance between these groups can be optimized. The surroundings of the functional groups can also be prepared with a view to maximally efficient directed immobilization.

In a particularly preferred embodiment of the invention, the inorganic carrier, for example the carrier in the form of quartz, diatomaceous earth, kieselguhr, silica gel and/or $SiO_2$ powder is silanized, preferably after previous hydrophilization, before bringing out the functional groups 1 A and 1 B.

In a particularly preferred embodiment it is possible to provide for the number of functional groups 1 A and 1 B on the surface to be variable through addition of diluent silanes in the preferably provided silanization. The term diluent silane means an organosilane which has biochemically inert functional groups and which is moreover unable to bind a spacer carrying the functional surface groups. The diluent silane is preferably employed in order to, besides the diluent effect, also to reduce the nonspecific binding of proteins to the surface of the carrier. In a preferred embodiment, the diluent silane has, starting from the silane head group, 2 to 20 alkylene groups to which preferably 2 to 6 oxoethylene groups are attached and are terminated by, for example, a hydroxy group or methyl ether group.

A particularly preferred embodiment provides for the diluent silanes on the carrier surface to favor the self-assembly effect through an appropriate alkyl chain length. It is additionally possible to provide for these diluent silanes used in the silanization of the carrier to reduce the nonspecific adsorption of proteins on the nanoparticle surface through added appropriate functional units such as, for example, oligoethylene glycol units. It is also possible according to the invention to employ other chemical compounds as long as they have a protein-repelling effect in relation to their nonspecific binding characteristics.

The invention provides for the nanoparticles, especially the surface, to have additional functionalities. It is possible according to the invention for the carrier to have in particular fluorescent labels, UV/Vis labels, superparamagnetic functions, ferromagnetic functions and/or radioactive labels. It is possible on the basis of the functionalities employed according to the invention for correspondingly equipped nanoparticles easily to be detected and/or isolated using suitable devices.

The surface of the nanoparticle carrier can, however, according to the invention also have additional chemical compounds. These additionally attached chemical functionalities depend inter alia on the later use of the nanocytes of the invention. If they are to be used for example for the therapy and/or diagnosis of diseases, the nanoparticles may comprise suitable chemical compounds with therapeutic and/or diagnostic effect. A particularly preferred embodiment provides for the nanoparticles of the invention additionally to comprise medicinal substances such as cytostatics. They are accordingly particularly suitable for the therapy of neoplastic diseases.

However, it is also possible to provide according to the invention for the functionalization of the carrier to take place using one or more chemical compounds which serves for steric stabilization and/or for preventing a conformational change of immobilized TNF and/or for preventing the attachment of a further biologically active compound to the carrier. It is particularly preferred according to the invention for this chemical compound to be a polyethylene glycol, an oligoethylene glycol, dextran or a mixture thereof.

The carrier may, besides additional chemical functions, also comprise further biological functions. This further preferred embodiment carries ligands, for example-peptides or proteins, on its surface which specifically bind selected tissues or cells.

The TNF molecule to be immobilized can according to the invention be of natural or synthetic origin. It may also have been modified by comparison with the wild-type protein by methods of genetic manipulation, and/or comprise unnatural and/or unusual amino acids.

In a preferred embodiment of the present invention, the TNF molecule to be immobilized is prepared by methods of peptide synthesis or by in vitro translation. Moreover, in a preferred embodiment, unnatural, preferably linker-spacer-carrying, amino acids are deliberately incorporated during the preparation, so that directed TNF immobilization compatible with retention of the biological TNF activity on the carrier is subsequently possible. Application of the principle of incorporating unnatural amino acids moreover makes deliberate and selective incorporation of fluorophores or other markers possible on these unnatural amino acids.

It is possible in a particularly preferred manner for these modifications to consist of replacing naturally occurring amino acids in the TNF molecule by unnatural amino acids, i.e. deleting an amino acid which occurs naturally in a particular position, and inserting an unnatural amino acid at the same place. Introduction of an unnatural amino acid can take place by introduction of a stop codon at the desired place, through the use or insertion of a suppressor tRNA loaded with the appropriate unnatural amino acid, and of an in vitro translation approach carried out therewith. Such unnatural amino acids are compounds having an amino acid function and a radical R and not being defined by a naturally occurring genetic code, for example L-(6,7-dimethyloxycoumaryl)alanine. It is preferred for these amino acids to have an alkyl ketone group or an aldehyde group, thioester group, thiol group, hydrazine group or hydrazide group. These unnatural amino acids can be introduced into the molecule by methods of genetic manipulation or during a chemical synthesis of TNF, preferably together with a spacer or linker.

Thus, in a particularly preferred embodiment of the invention, at least one amino acid of TNF is derivatized, in particular by introducing an alkyl ketone group, thiol group, aldehyde group, thioester group, hydrazine group and/or hydrazide group. In particular, one of the foregoing functions is connected via a spacer to the side chain of a natural or unnatural amino acid, or the spacer has such a function. The spacer can in a preferred embodiment be flexible or linear and have for example a chain length of from 2 to 50 atoms. The spacer in a further preferred embodiment is formed by optionally substituted and/or heteroatom-containing alkylene groups.

In a further preferred embodiment, the spacer is formed by the binding of a side chain of an amino acid of TNF, for example lysine, to levulinic acid (4-oxopentanoic acid), with simultaneous introduction of a methyl ketone group and formation of the spacer accordingly from side chain and levulinic acid.

Where the unnatural amino acid to be employed already has an alkyl ketone group, aldehyde group, thiol group, thioester group, hydrazide group or hydrazine group, the aforementioned derivatization is no longer necessary. It is thus possible to provide for a naturally occurring amino acid, for example lysine, to be modified for example by derivatization of its side chain, in particular its primary amino group, with the carboxylic acid function of levulinic acid. TNF molecules which have such a naturally occurring amino acid with unnatural derivatization are modified within the meaning of the present teaching. Incorporation of, for example, levulinic acid into an unnatural or natural amino acid makes it possible to incorporate, at a defined space in the sequence, a keto function which can then react selectively for example with a hydrazine or hydrazide to give hydrazone.

In a further preferred embodiment of the present invention, TNF is modified by introducing tags, i.e. labels, especially by means of three histidine residues, preferably oligohistidines, into the TNF molecule, preferably at the C terminus or N terminus. However, intramolecular disposition of such tags is also possible. An embodiment of this type provides for the surface of the carrier, for example the silanized surface of the carrier, to be provided with functional groups by attaching metal chelate complexes. This results in non-covalent binding of the metal chelate complexes to the oligohistidine residue of the TNF molecule to be immobilized. In a particularly preferred embodiment of the invention, the metal component of the metal chelate complex is a divalent metal cation, in particular nickel$^{2+}$. In a particularly preferred embodiment, the metal chelate complex is nickel-NTA (NTA: nitrilotriacetic acid), in particular a derivative thereof. The metal chelate complex, in particular Ni-NTA or a derivative thereof, is in a preferred embodiment bound to the surface of the carrier, for example by means of a binding between a primary amino group of the NTA derivative and a surface-bound epoxy group.

It is also possible to provide according to the invention for undertaking the modification of TNF by attaching to the latter preferably at the C terminus or N terminus at least one Strep tag, for example Strep tag I or Strep tag II or biotin or desthiobiotin. In connection with the present invention, a "Strep tag" also means functional and/or structural equivalents as long as streptavidin and/or its equivalents are able to bind. The term "streptavidin" thus includes for the purposes of the present invention also its functional and/or structural equivalents. This embodiment provides for the surface of the carrier, preferably of an inorganic carrier, in particular the silanized surface of the carrier, to be provided with streptactin, avidin, neutravidin or streptavidin. The binding provided according to the invention between TNF molecules to be immobilized and the surface of the carrier thus takes place by an affinity binding between, for example, Strep tag and, for example, streptavidin. It is also possible to provide for example streptavidin on the TNF molecule and for example the Strep tag as functional group of the carrier. It is, of course, also possible according to the invention to undertake more than one of the modifications mentioned on the TNF molecule to be immobilized, for example to introduce an unnatural amino acid which comprises oligohistidine and/or Strep tags.

The invention thus provides for bringing about the binding of TNF molecules which have, for example, been modified by unnatural amino acids, natural but unnaturally derivatized amino acids, specific histidine and/or Strep tags, with reactive surfaces complementary thereto in such a way that suitable attachment of the TNF molecules and thus immobilization thereof takes place.

The present invention also relates to TNF molecules themselves which are modified as described above.

In an advantageous manner, bound TNF completely retains its biological functions in these circumstances. The linkers or spacers which are provided between carrier surface and TNF surface satisfy the steric requirements for immobilization of TNF with retention of its activity. In addition, the invention also makes the site-specific incorporation of reporter or marker groups, for example fluorophores, spin labels, gold particles for light scattering etc., possible in positions which do not impair the functional properties of TNF. The advantages of the nanoparticles of the invention and of the method of the invention for the specific and directed immobilization and labeling of TNF compared with the prior art result from the specific chemical reactions between TNF molecules which have been modified with unnatural amino acids or specific groups, and solid phases with complementary reactivity, and from the selective modification of the TNF molecule to be immobilized. The immobilized and, where appropriate, also labeled TNF molecules are, owing to the retention of their natural conformation, more stable toward enzymatic or chemical degradation and retain their biological functions. Moreover, in particular, the biological activities based on protein-protein interaction are passed on by the immobilized TNF molecules.

A further preferred embodiment of the invention provides for the TNF molecule to be labeled with markers which allow it to be detected. Possible examples thereof are fluorophores, spin label, gold particles, radioactive markers or the like. It is particularly preferred for these markers, for example the fluorophores, to be able to show a specific change in the fluorescence emission when a binding partner which is to be detected in an assay binds to the bound TNF molecule. The fluorophores can be introduced into the TNF to be immobilized by means of amino acids, in particular unnatural amino acids. Examples of fluoromarkers suitable according to the invention are N-methylazatryptophan or coumarin derivatives such as DCA (6,7-dimethoxy-4-coumaryl) or NBD (N-β-7-nitrobenzofurazan-L-N-diaminopropionic acid). The TNF molecule to be immobilized can also be labeled with fluorophores which make single-molecule detection possible, for example the fluorescent dyes CyDye (Ammersham Pharmacia Freiburg) or Alexa (Molecular Probes, Eugene, USA).

The detection which is made possible by the invention of surface-bound ligands of the immobilized TNF molecule, i.e. for example the detection of a cell surface receptor, can take place for example by matrix-assisted laser desorption/ionization mass spectrometry (MALDI-TOF). The mass spectroscopic detection includes the identification and characterization of the bound ligand in situ, and spatially resolved analysis. The detection of surface-bound ligands is possible by fluorescence spectroscopy. The binding of the ligand to the solid-phase ligand immobilized according to the invention, i.e. TNF, elicits a change in the fluorescence properties of the fluorescent markers employed according to the invention, making it possible to quantify the binding events.

The present invention thus also relates to acids for detecting an interaction of immobilized TNF with, for example, ligands such as receptors, functional or structural equivalents, analogs, agonists, antagonists or the like, in particular for the purpose of medical research and diagnosis, employing the nanoparticles of the invention in order to identify the aforementioned binding partners of immobilized TNF. In this method, nanoparticles of the invention, with TNF immobilized thereon, are brought into contact with a solution to be investigated, which contains potential binding partners, and an interaction or an inhibition of this interaction is detected. The aforementioned method thus also represents a method for identifying or screening potential binding partners, for example potential ligands, of the TNF immobilized according to the invention.

The invention likewise relates to methods for the quantitative isolation of substances which react, i.e. bind, with the TNF molecule immobilized according to the invention. Such substances are in particular proteins.

It is possible in a particularly preferred manner to employ the methods of the invention and the nanoparticles of the invention also for identifying substances which act for example as modulators, i.e. enhancers, inducers or inhibitors, of the, in particular physiological, interactions of TNF with other proteins. Such inhibitors to be detected can be, for example, genetically modified, endogenous proteins, synthesized chemical compounds from substance libraries or other, even unknown, substances which may where appropriate be associated with therapeutic benefits.

A further embodiment can provide for the immobilization of TNF which carries or represents a first of two reactants, and detects the interaction of the second reactant with the first reactant by a suitable detection method. In this connection it also possible advantageously to provide for the interaction of the second reactant with the first reactant to be detected in the presence or absence of a potential modulator, for example inducer or inhibitor, by suitable detection methods and thus potential inducers or inhibitors can be examined for their activity, for example as medicaments. The potential inducers or inhibitors may originate for example from substance libraries. It is possible to provide in a particularly preferred embodiment for the inhibitor or the second reactant, i.e. for example a protein, to be a protein identified in genome sequencing projects.

The present invention thus also relates to methods for identifying and/or detecting a substance able to modify, in particular promote or inhibit, the interaction between immobilized TNF and its interacting partner, wherein the TNF immobilized on nanoparticles is incubated together with a, preferably purified and isolated, interacting partner in the presence or absence of the substance to be tested, and an effect of this substance on the interaction between immobilized TNF and its binding partner is detected.

The present invention also relates to methods for the directed immobilization of TNF on a nanoparticle with retention of the biological TNF activity, where the surface of an inorganic or organic carrier is modified by attaching a first functional group 1 A and, where appropriate, a second functional group 1 B, and modified TNF molecules having complementary functional groups 2 A and, where appropriate, functional groups 2 B are brought into contact with the modified nanoparticle surface in such a way that a covalent bonding between functional groups 1 A and 2 A and, where appropriate, a non-covalent binding between groups 1 B and 2 B takes place in such a way that the protein binds in a directed fashion and with retention of its biological activity to the nanoparticles.

The invention provides in particular for functional groups 1 A and 2 A to be selected from the group consisting of amino group, carboxy group, epoxy group, maleimido group, alkyl ketone group, aldehyde group, hydrazine group, hydra-zide group, thiol group and thioester group. Functional groups 1 B and 2 B are selected according to the invention from the group consisting of oligohistidine group, Strep tag I, Strep tag II, desthiobiotin, biotin, chitin, chitin derivatives, chitin binding domain, metal ion chelate complex, streptavidin, streptactin, avidin and neutravidin. It is possible according to the invention for functional groups 1 A, 1 B, 2 A and/or 2 B to be connected to the carrier and/or protein with use of a spacer.

In a preferred embodiment, the functional groups 1 A and 1 B are attached to the carrier surface by means of graft polymerization, silanization or chemical derivatization. For example, after preparation of the carrier it can be first hydrophilized and then silanized. The carrier surface is silanized for example using an organosilane, in particular $SiR_1R_2R_3R_4$, where $R_1$ to $R_3$ are hydrolyzable groups such as alkoxy groups or halides, preferably chlorides, and $R_4$ is an organic radical which can be designed as spacer with first functional group 1 A or as binding site for a spacer having the first functional group 1 A. When, in another embodiment of the invention, $R_4$ is designed as binding site, for example as epoxy group, for the spacer having the functional group, the silanization is followed by attachment of the functional groups to the surface, i.e. for example the maleimido group etc.

The density of the functional groups or the distance of the functional groups from the surface, and thus the flexibility, can be optimized where appropriate. The invention provides for the environment of the functional groups on the carrier surface to be prepared in terms of electrostatic and steric provisions for maximally efficient, directed immobilization. It is moreover possible for the carrier surfaces to be additionally equipped with molecules such as polyethylene glycols, oligoethylene glycols, dextrans and the like in order to prevent an unwanted conformational change of the immobilized TNF molecules, to minimize the nonspecific adsorption of other biological compounds and/or to stabilize the carrier systems sterically.

In a further step, TNF is immobilized on the modified surface of the nanoparticle carrier, it being necessary to choose the appropriate protein modification depending on the surface modification. The TNF molecule to be immobilized is moreover brought into contact according to the invention with the modified surface under conditions such that degradation of the protein is minimized or prevented.

After immobilization of the TNF on the carrier surface, the invention provides for the nanoparticles of the invention to be masked, where appropriate with the aid of a stealth method, in particular by packaging in, for example, liposomes, in order to achieve an adequate biological circulation on later use of the nanoparticles of the invention.

There is also the possibility according to the invention of depositing the nanoparticles, with TNF immobilized thereon, on a membrane, in which case the resulting film is mechanically and/or chemically stabilized by crosslinking.

The present invention also relates to the use of the nanoparticles of the invention for preparing a pharmaceutical composition, in particular for chemotherapy. In connection with the present invention, a "pharmaceutical composition" means a mixture used for diagnostic, therapeutic and/or prophylactic purposes and comprising natural or synthetically prepared active ingredients in a form which can be readily administered to the patient. Thus, the invention provides that the pharmaceutical composition to be prepared comprises the active ingredient, in particular TNF, in a form immobilized on a nanoparticle. The pharmaceutical composition may be a solid or liquid mixture. A pharmaceutical composition may comprise where appropriate one or more pharmaceutical carriers and further additives such as stabilizers, thickeners, release agents, lubricants, colors, odorants, flavorings, bulking agents, emulsifiers or the like.

The present invention also therefore relates to a pharmaceutical composition which comprises the nanoparticles of the invention, i.e. which comprises TNF in immobilized form on a nanoparticle of the invention.

Further advantageous embodiments of the present invention are evident from the dependent claims.

The invention is explained in more detail by means of the figures and the following examples.

Sequence Listing:
SEQ ID No. 1 shows the coding DNA sequence of a TNF fusion protein for the example of CysHisTNF (construct 1) with nucleotides 1 to 546;
SEQ ID No. 2 shows the translated amino acid sequence, derived from SEQ ID No. 1, of amino acids 1 to 181;
SEQ ID No. 3 shows the coding DNA sequence of a TNF fusion protein for the example of TNC-TNF (construct 2) with nucleotides 1 to 705, and
SEQ ID No. 4 shows the translated amino acid sequence, derived from SEQ ID No. 3, with amino acids 1 to 234.

The figures show

FIG. 8 shows the results of waveguide spectroscopy resonance analyses where the modified tumor necroscopy factor receptor 1 (TNFR1-Fc) was immobilized via α-amino groups on a carboxymethyldextran matrix (CMD matrix) and then binding studies were carried out with CyHISTNF. Plotting the extent of binding of CysHisTNF (extent) against the concentration employed (ligate) results in a binding curve which, in the saturation region, describes the maximum possible binding (Bmax). Plotting the ratio of the extent of binding and the CysHisTNF concentration (extent/ligate) against the extent of binding (extent) results in a line equation whose gradient corresponds to the negative affinity constant $K_D$ (Scatchard plot). Plotting the association rate constant (con) against the CysHisTNF concentration is a further method for determining the $K_D$ and serves to determine the measured $K_D$. The intercept of the line with the Y axis corresponds to the half-life $t_{1/2}$ of the ligand-receptor complex and is thus a measure of the stability of the CysHisTNF-receptor complex.

FIG. 9 shows the results of waveguide spectroscopy resonance analyses where the modified tumor necrosis factor receptor 2 (TNFR2-Fc) was immobilized via α-amino groups on a CMD matrix and then binding studies were carried out with CyHISTNF. Plotting the extent of binding of CysHisTNF (extent) against the concentration employed (ligate) results in a binding curve which, in the saturation region, describes the maximum possible binding (Bmax). The intercept of the line with the Y axis corresponds to the half-life $t_{1/2}$ of the ligand-receptor complex and is thus a measure of the stability of the CysHisTNF-receptor complex.

FIG. 10 shows the results of waveguide spectroscopy resonance analyses where the modified tumor necrosis factor receptor 1 (TNFR1-Fc) was immobilized via α-amino groups on a CMD matrix and then binding studies were carried out with TNF. Plotting the extent of binding of TNF (extent) against the concentration employed (ligate) results in a binding curve which, in the saturation region, describes the maximum possible binding (Bmax). The intercept of the line with the Y axis corresponds to the half-life $t_{1/2}$ of the ligand-receptor complex and is thus a measure of the stability of the TNF-receptor complex.

FIG. 11 shows the results of waveguide spectroscopy resonance analyses where the modified tumor necrosis factor receptor 2 (TNFR2-Fc) was immobilized via α-amino groups on a CMD matrix and then binding studies were carried out with TNF. Plotting the extent of binding of TNF (extent) against the concentration employed (ligate) results in a binding curve which, in the saturation region, describes the maximum possible binding (Bmax). The intercept of the line with the Y axis corresponds to the half-life $t_{1/2}$ of the ligand-receptor complex and is thus a measure of the stability of the TNF-receptor complex.

Figure 12:
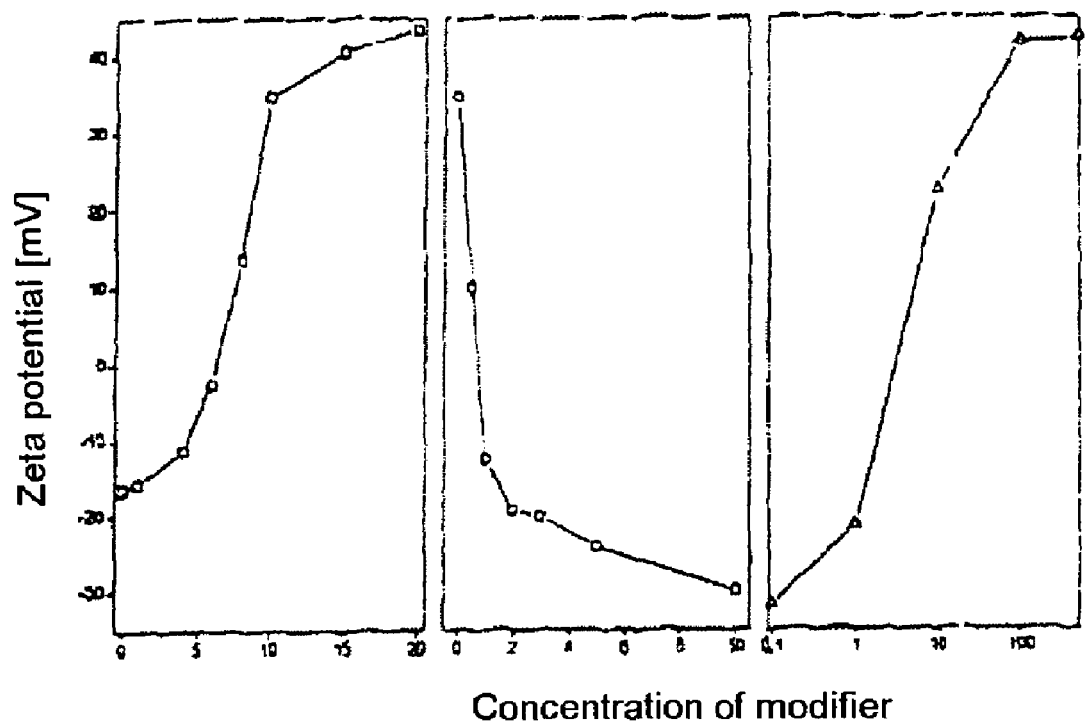

FIG. 12 shows the results of zeta potential investigations.

EXAMPLE 1

Preparation of a Carrier 1.1 Silica Carrier 12 mmol of tetraethoxysilane and 90 mmol of $NH_3$ were added to 200 ml of ethanol. The mixture was stirred at room temperature for 24 hours and then the particles which had formed were purified by multiple centrifugation. This resulted in 650 mg of silica particles with an average particle size of 125 nm.

1.2 Magnetic Iron Oxide Carrier 200 ml of a 1 M $FeCl_3$ solution and 5 ml of a 2 M $FeSO_4$ solution in 2 M HCl were added with vigorous stirring to 250 ml of a 0.7 M $NH_3$ solution. The mixture was then stirred for 30 minutes, and the black solid which had formed was washed with 200 ml of water. The precipitate was subsequently stirred with 100 ml of 2 M $HNO_3$ for 30 minutes and washed three times with 100 ml of water each time. The superparamagnetic iron oxide carriers were resuspended in 50 ml of a 0.1 M tetramethylammonium hydroxide solution. This resulted in 2 g of iron oxide particles with an average particle size of 10 nm.

1.3 Magnetic Composite Carrier 50 mg of the magnetic iron oxide particles obtained in Example 1.2 were washed twice with 5 ml of ethanol and then taken up in 200 ml of ethanol. 12 mmol of tetraethoxysilane and 90 mmol of $NH_3$ were added to the solution. It was subsequently stirred at room temperature for 24 hours. The particles were then purified by multiple centrifugation. This resulted in 600 mg of magnetic composite particles with an average particle size of 150 nm.

1.4 Fluorescent Carriers

190 μmol of fluoresceinamine and 170 μmol of isocyanato-propyltriethoxysilane in 50 ml of ethanol were boiled under reflux for 3 hours. 3 mmol of tetraethoxysilane and 880 μl of a silane-dye solution were added to 50 ml of ethanol. Addition of 22.5 mmol of $NH_3$ was followed by stirring at room temperature for 24 hours. The resulting particles were then purified by multiple centrifugation. This resulted in 160 mg of silica particles with an average particle size of 110 nm.

1.5 Organic Polymeric Carriers 50 mg of the emulsifier p-(11-acrylamido)undecenoyloxyphenyl-dimethylsulfonium methyl sulfate were dissolved in 30 ml of water with stirring. Argon was subsequently passed through the solution for one hour. While stirring, 1.8 ml ml of methyl methacrylate were then added. The resulting emulsion was heated to 60° C. The polymerization was started by adding 10 mg of 2,2'-azobis(2-amidinopropane) dihydrochloride. After hours, the particle suspension was cooled and the particles were purified by centrifugation. This resulted in 1.6 g of particles with an average particle size of 145 nm. The resulting particles have covalently linked sulfonium groups on their surface (zeta potential in phosphate buffer, pH 7.0: +22 mV) and are able to bind nucleophiles.

EXAMPLE 2

Surface Modification of the Carriers 2.1 Aminio-functionalized Surface

A 1% by weight aqueous suspension of the carriers obtained in Examples 1.1 to 1.4 was mixed with 10% by volume of 25% ammonia. 20% by weight of aminopropyltriethoxysilane, based on the carriers, were added and the mixture was stirred at room temperature. The particles were purified by multiple centrifugation. The resulting particles have functional amino groups on their surface (zeta potential in 0.1 M acetate buffer: +35 mV).

2.2 Amino-functionalized Organic Polymeric Carriers 10 mg of the carriers obtained in Example 1.5 were put into 50 µl of a 10 mmol phosphate buffer (pH 7.8). Then 950 µl of a 1 M ethylenediamine solution in 10 mmol phosphate buffer (pH 7.8) were added. The mixture was then shaken at room temperature for 2 hours. The particles were then purified by centrifugation. The carriers obtained in this way have covalently bonded amino groups on their surface.

2.3 Carboxy-functionalized Surface

Firstly a 2% by weight suspension of amino-functionalized carriers in tetrahydrofuran was prepared. 260 mg of succinic anhydride were added to 10 ml of this solution. Ultrasound treatment for 5 minutes was followed by stirring at room temperature for one hour. The carriers were then purified by multiple centrifugation. The resulting silica carriers have functional carboxy groups (zeta potential in 0.1 M acetate buffer: −35 mV) on their surface and have an average particle size of 170 nm.

2.4 Carboxydextran-modified Carriers 10 mg of amino-functionalized nanoparticles and 1 mg of carboxydextran (Sigma, >55 cps) were added to 1 ml of 0.1 M morpholinoethanesulfonic acid buffer (MES, pH 5.0). Then 30 µl of an N-ethyl-N'-(3-dimethylaminopropyl)carbodiimide (EDC) solution with a concentration of 500 mmol/ml were added. The mixture was subsequently shaken at room temperature for 30 minutes. The carriers were washed alternately with MES buffer and TBE buffer (89 mM tris(hydroxymethyl)aminomethane, 89 mM boric acid, 2 mM ethylenediaminetetraacetic acid, pH 8.3). The washed particles were subsequently taken up in 1 ml of MES buffer. The resulting silica particles have functional carboxy groups (zeta potential in 0.1 M acetate buffer: −25 mV) on their surface and have an average particle size of 160 nM. This dextran surface is particularly suitable for immobilizing proteins whose tertiary structure is deranged by adsorption processes on the carrier surface.

2.5 Amino Functionalization of carboxy(dextran) Carriers

Firstly a 1 M ethylenediamine solution in 0.1 M MES buffer (pH 5.0) was prepared. 500 µg of the carboxy(dextran)-modified carriers and 30 µl of a 500 µmol/ml EDC solution in MES buffer were added thereto. The mixture was subsequently shaken at room temperature for 3 hours. The carriers were then washed several times with MES buffer. This resulted in carriers with an average particle size of 160 nm and a zeta potential of +25 mV in 0.1 M acetate buffer.

It is also possible to employ other amines in an analogous manner to vary the length of the spacer or the density of the functional groups, for example 4,7,10-trioxa-1,13-tridecanediamine (or higher homologs) or tris(2-aminoethyl)amine.

2.6 Nitrilotriacetic Acid (NTA) Surface 10 mg of carboxy-modified carriers were washed twice with 1 ml of acetonitrile (MeCN) and then taken up in 1 ml of MeCN. To this were added 10 mmol of dicyclohexylcarbodiimide and 10 µmol of N-hydroxysuccinimide. This was followed by shaking at room temperature for two hours. Washing was then carried out once with 1 ml of cyclohexane and once with 1 ml of MeCN. The particles were then taken up in 1 ml of MeCN. 4 µmol of N,N-biscarboxymethyl-L-lysine were added thereto and shaken at room temperature for three hours. This was followed by washing once with 1 ml of acetonitrile and twice with 1 ml of 10 mM phosphate buffer (pH 7.0).

This reaction firstly increases the density of the functional carboxy groups and secondly $Ni^{2+}$ ions can be bound by complexation with this surface. This surface is then able to bind proteins modified with His tags.

2.7 Pegylated Particles 1 mg of amino-functionalized particles (Examples: 2.1, 2.2, 2.5) are suspended in 1 ml of 10 mM phosphate buffer (pH: 7.0). Subsequently, up to 1 mg of heterofunctional polyethylene glycols (such as mPEG-succinimidyl propionate, t-Boc-NH-PEG-succinimidyl propionate, maleimido-PEG-succinimidyl propionate or mixtures thereof) are added, and the mixture is shaken at room temperature for 3 hours. If protective groups are present on the surface they are removed by treatment with 1% trifluoroacetic acid for 2 hours. The particles are washed twice with 1 ml of 10 mM phosphate buffer (pH: 7.0).

The surfaces are suitable for avoiding nonspecific attachment of proteins.

If these surfaces have amino groups after deblocking of the protective groups, they can be used further in Example 2.9.

2.8 Thiol Surface 10 mg of carboxy-modified carriers were washed twice with 1 ml of acetonitrile (MeCN) and then taken up in 1 ml of MeCN. 10 µmol of dicyclophexylcarbodiimide and 10 µmol of N-hydroxysuccinimide were added thereto and then shaken at room temperature for two hours. This was followed by washing once with 1 ml of cyclohexane and once with 1 ml of MeCN. The carriers were then taken up in 1 ml of MeCN. 500 µg of cysteine were added thereto and shaken at room temperature for 3 hours. This was followed by washing once with 1 ml of acetonitrile and twice with 1 ml of 10 mM phosphate buffer (pH 7.0).

This surface is particularly suitable for immobilizing proteins via disulfide bridges.

2.9 Maleimido-activated Surface

500 µg of amino-functionalized carriers were resuspended in 1 ml of 10 mM phosphate buffer (pH 7.0). 1.25 µmol of sulfo-succinimidyl 4-(N-maleimidomethyl)cyclohexane-1-carboxylate were added thereto and shaken at room temperature for one hour. This was followed by washing with cold 10 mM phosphate buffer (pH 7.0), and the carriers were taken up in 1 ml of 0.1 M phosphate buffer (pH 7.0).

2.10 Iodoacetyl-activated surface

500 μg of amino-functionalized carriers were resuspended in 1 ml of 10 mM phosphate buffer (pH 7.0). 1.25 μmol of succinimidyl (4-iodoacetyl)aminobenzoate were added thereto and shaken at room temperature for one hour. This was followed by washing with cold 0.1 M phosphate buffer (pH 7.0), and the carriers were taken up in 1 ml of 10 mM phosphate buffer (pH 7.0).

These surfaces are suitable for coupling on proteins having free thiol groups.

2.11 Surface With $NH_2$ and COOH Groups

The covering with functional groups is described in Examples 2.1 to 2.9 in such a way that it proceeds quantitatively. These coverings can, however, normally also be controlled through the choice of the reaction conditions, especially via the concentration of the modifying agent, so that they take place only partly. An appropriate choice of the modifying agents results in different functional groups being present side by side on the carrier surface.

For example the concentration of succinic anhydride in Example 2.3 is reduced. A suitable choice of the $NH_2$/COOH ratio varies the isoelectric point of the carrier system in a wide range, for example between 8 and 3. This is a crucial parameter on reaction with proteins to control the reactivity, because systems having the same charge repel one another.

2.12 Clustering

The first graph shows the reaction of unmodified silica particles with aminosilanes (in analogy to Example 2.1.). In the second graph, these amino-functionalized surfaces are reacted with succinic anhydride (in analogy to Example 2.3.). The carboxy groups resulting therefrom on the particle surface can be reacted further for example with ethylenediamine, as is to be seen in graph 3 (in analogy to Example 2.5.). Amino-functionalized surfaces result once again. The zeta potential and thus the density of the functional groups on the particle surface can be controlled by varying the modifier concentration.

2.13 Carrier Surfaces With SH and NTA Groups

The reaction is carried out as in Examples 2.6 or 2.7, although employing a mixture of the two modifying agents. Proteins with His tags are non-covalently aligned thereby in a first step, and this state is subsequently fixed permanently by forming a covalent disulfide bridge.

3. Immobilization of TNF on Nanoparticles

The surface-modified nanoparticles prepared above were used to immobilize TNF molecules. In these cases, the TNF molecules were coupled in a directed manner, with retention of their ability to signal, onto the inert carriers so that on use of the nanoparticles an interaction with a TNF receptor was possible and the signal response of the cell was measurable in defined cell systems.

3.1 Construction of TNF Variants 3.1.1 TNF Fusion Proteins With N-Terminal Modifications (Construct 1)

The linker-modified fusion protein CysHisTNF which has, in the vicinity of the N terminus, a reactive thiol group which is able for example to enter into a covalent bonding with a maleimido group on the surface of nanoparticles was constructed. The protein was additionally provided with a Gly-rich linker with a His tag consisting of two or more histidine residues, thus making it possible on the one hand for the protein to be bound to an $Ni^{2+}$ loaded affinity matrix and eluted with imidazole. On the other hand, the His tag permits non-covalent binding of CysHisTNF to metal ion chelate complexes, especially nickel nitrilotriacetic acid (NTA) groups on the surface of nanoparticles. Cloning of the functional protein took place by standard methods, for example using methods for site specific mutagenesis, and is disclosed in detail hereinafter. The DNA sequence is depicted in SEQ ID No. 1 with nucleotides 1 to 546. The relevant amino acid sequence with amino acids 1 to 181 is depicted in SEQ ID No. 2.

The resulting structure from the N terminus to the C terminus is as follows:

1. Sequence of linker 1 (L1): poly-Gly linker with a Cys (NT 25-27, AA 9) and a His tag (NT 43-60, AA 15-20): NT 1-76, AA 1-26
2. TNF module: mature form of the human TNF protein (17.5 kDa form, recombinant TNF, Swissprot #PO1375, AA 1-157) with deletion of the N-terminal 2 AA (TNFdelta 1,2): NT 79-543, AA 27-181
3. Stop codon: NT 544-546

Construction of the linker-modified fusion protein having a reactive thiol group at the N terminus and having a (His) 6 tag for purification (SEQ ID No. 1) is described below.

This fusion protein (abbreviated to: CysHisTNF) was prepared as follows:

The TNS fragment (AA 3-181) was cut out of another construct PinPointHisTNF (Pinpoint™ Xa-3 prokaryotic vector, described in "PinPoint™ Xa Protein Purification System", Promega) by restriction digestion of the plasmid DNA with SacI and HindIII. The fragment isolated after preparative agarose gel electrophoresis with DNA elution was inserted into a modified vector (pQE 5, QIAexpress®, Qiagen). The latter had previously been digested with BamHI and HindIII.

The construct was sequenced to verify the cDNA sequence.

The construct obtained in this way permits prokaryotic expression of the CysHisTNF fusion protein. This expression was carried out substantially as stated by the manufacturer (QIAexpress® system, Qiagen). No IPTG was added to induce expression (baseline induction).

The bacterial lysate (cytoplasmic extract) was employed for the concentration. The TNF protein was purified by affinity chromatography (IMAC, HiTrap® affinity column, Amershampharmacia biotech). The protein was bound to an $Ni^{2+}$ loaded affinity matrix and eluted with imidazole as stated by the manufacturer.

FIG. 1 depicts the result of the investigation in relation to the induction of apoptosis in TNF-sensitive tumor cell lines. The figure shows that the TNF fusion protein CysHisTNF has high bioactivity. FIG. 1 shows cells of the human rhabdomyosarcoma line KYM-1. These were cultivated at 37° C. as described in Grell et al., 1995, and Grell et al., 1994. For the bioassay, $1\times10^4$ samples/well were seeded in 96-well microtiter plates and incubated under culturing conditions overnight. The cells were then cultivated in the presence of titrated concentrations of human recombinant TNF-α (▲) or CysHisTNF [bacterial lysate (■), purified protein (▼)] for 16-20 h, and the metabolic cell activity was quantified in an MTT assay (Grell et al., 1995). The extinction was determined at 550 nm. The means from a typical experiment±SD are depicted in each case.

3.1.2 TNF Fusion Proteins With Natural Linkers (Multimerization Modules) (Construct 2)

A fusion protein with the multimerization domain from the tenascin C molecule (TNC) was constructed. The multimerization domain from this molecule permits specific covalent trimerization of the TNF fusion protein and comprises two cysteine residues at the N terminus. Cloning of this fusion protein took place by standard methods as described in detail hereinafter (Example 2). The DNA sequence is depicted in SEQ ID No. 3 with nucleotides 1 to 705. The relevant amino acid sequence with amino acids 1 to 234 is depicted in SEQ ID No. 4.

The resulting structure from the N terminus to the C terminus is as follows:
1. Sequence of linker 1 (L1): NT 1-24, AA 1-8
2. Trimerization domain of tenascin (chicken): NT 25-114, AA 9-38
3. Sequence of linker 2 (L2): NT 115-132, AA 39-44
4. TNF module: mutated form of the natural human TNF precursor protein (26 kDA membrane form, Swissprot #PO1375, 233 AA) with deletions of the N-terminal 56 AA and of AA 78-89 (TNF$_{delta\ 1-56,\ 78-89}$), i.e. deletion of the cytoplasmic domain, of the transmembrane domain and of the TACE cleavage site of the TNF precursor peptide: NT 133-627, AA 45-209
5. Sequence of liner 3 (L3): NT 623-645, AA 210-215
6. myc tag: NT 646-684, AA 216-228
7. His tag: NT 685-702, AA 229-234
8. Stop codon: NT 703-705

The fusion protein was expressed inter alia in prokaryotic cells, in particular in *E. coli*, mammalian cells and in the baculovirus expression system. TNF fusion proteins can be functionally expressed in mammalian cells as described in Wüest, T., 2001; Wüest et al., 2002, patent 2002, and in the baculovirus system.

As shown below, the TNF fusion protein TNC-TNF was also expressed prokaryotically.

EXAMPLE 2

(Construct 2)

Construction of a TNF fusion protein with the multimerization domain from the tenascin C molecule (AA 110-139, Swiss Prot. Accession No. P10039, chicken; or Swiss Prot. Accession No. P24821, human) (described in Wüest et al., 2002, patent WO 02/22833).

This domain with a so-called coiled-coil structure permits specific covalent trimerization of the TNF fusion protein and comprises two cysteine residues at the N terminus. The exact position of the thiol groups inside the protein sequence depends on the chosen expression system (different linker sequences). TNC-TNF contains 2 Cys at position 10 and 12 (SEQ ID No. 3).

Construct 2 was prepared as follows:

The TNC-TNF fragment (AA 9-234, see sequence 2) was cut out of a construct/plasmid pGD105TNC-TNF (eukaryotic expression vector pGD105, described in EP 0953 639) and subcloned into a prokaryotic vector.

For this purpose, plasmid DNA pGD105TNC-TNF was amplified using primers 1 and 2 and proof-reading PCR, thus introducing the Pst I and HindIII cleavage sites. The sequence section coding for the tenascin domain and the TNF domain was obtained by a PstI/HindIII digestion. The isolated fragment was inserted into the appropriate sites of the modified pQE-5 vector (Qiagen). The vector pQE-5 had previously been digested with PstI and HindIII.

All the cloning and PCR amplification steps took place by standard methods with the following primers. The construct was sequenced to verify the cDNA sequence.

Primer 1
5' AAC TGC AGC CTG TGG CTG TGC GGC TGC CCC AGA CAT CAA G 3'

Primer 2
5' CCC AAG CTT GGG TTA ATG ATG ATG GTG ATG 3'

The construct obtained in this way was expressed like construct 1 (Example 1). A difference from this was cultivation of the bacterial cells at 30° C. (without inducing expression).

Figure 2:
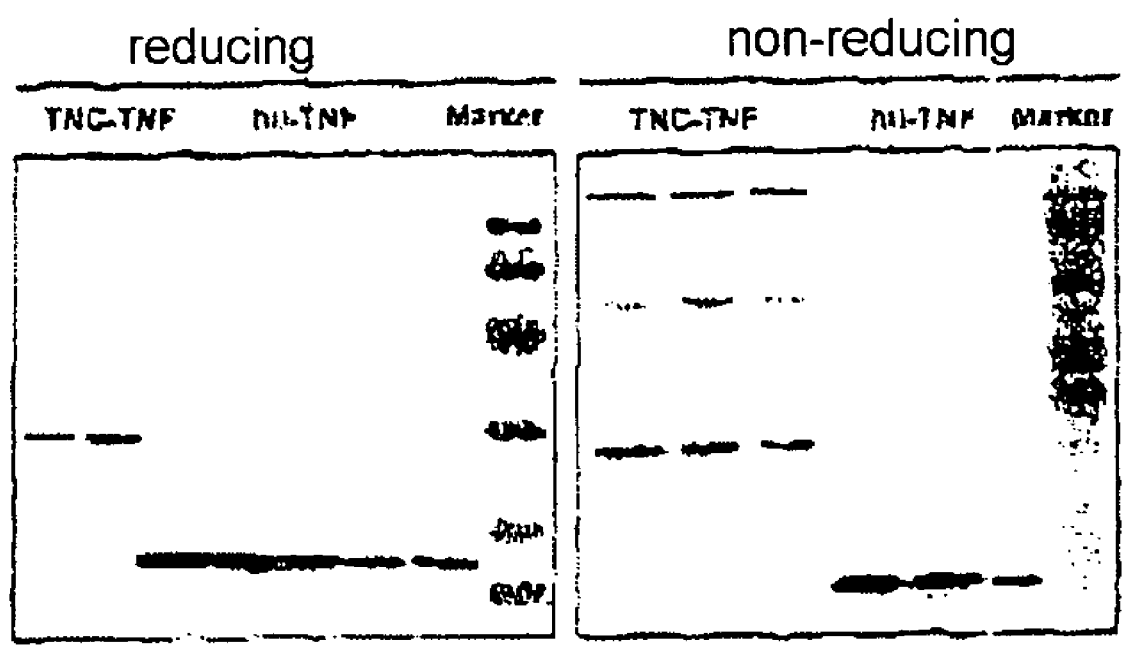
FIG. 2 shows the results of an electrophoresis.

FIG. 2 depicts the result of a gel electrophoretic fractionation after expression of the TNF fusion protein. The Western blot analysis shows that TNC-TNF organized as trimer is present under non-reducing conditions even with prokaryotic expression. Under reducing conditions, the protein migrates in accordance with the calculated MW of about 29 kDa for monomeric TNC-TNF.

TNC-TNF is purified as described in 3.1.1.

Figure 3:
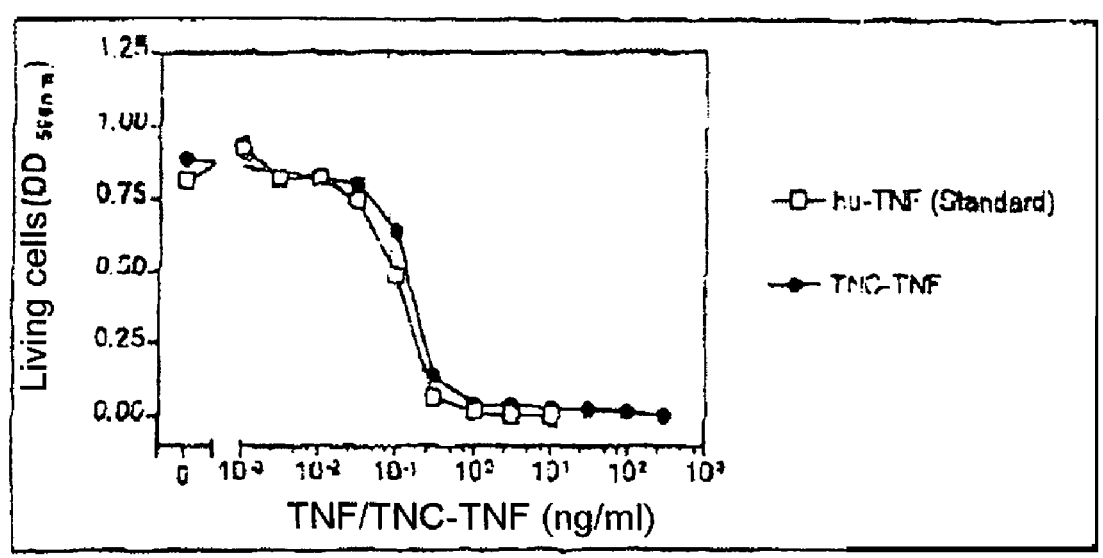
FIG. 3 shows the results of another bioassay with the KYM-1 target cell.

FIG. 3 depicts the result of the investigation of the induction of apoptosis in TNF-sensitive tumor cell lines. The figure shows that TNC-TNF has high biological activity.

Figure 1:
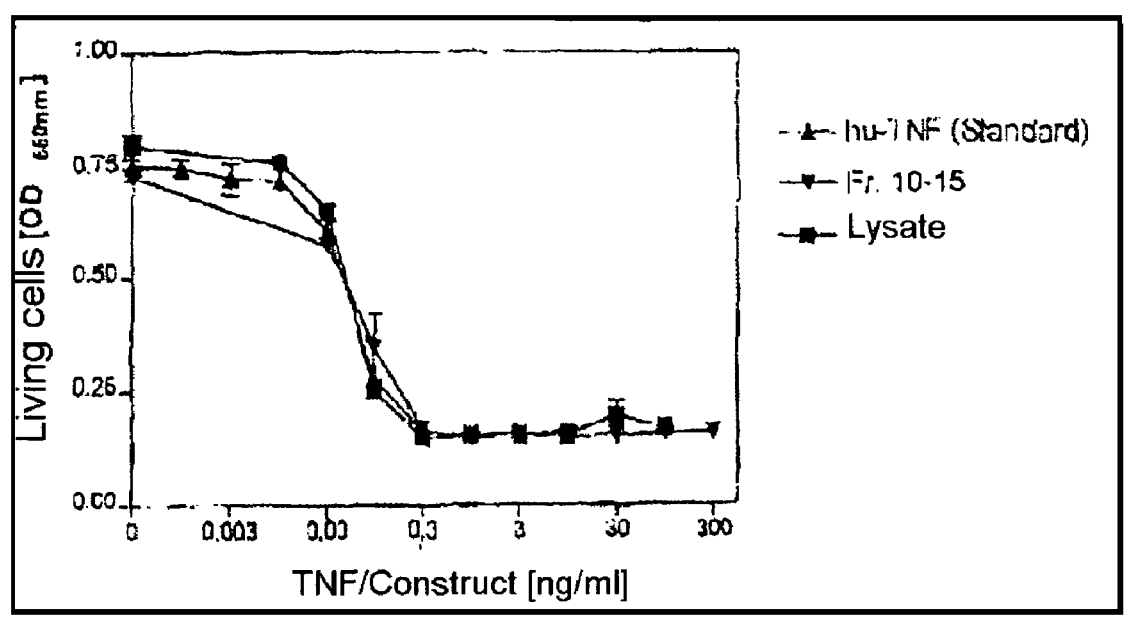
FIG. 1 shows the results of a bioassay with the KYM-1 target cell.

For the bioassay, the KYM-1 cells ($1.1 \times 10^4$ cells/well) were cultivated as described in FIG. 1. The cells were incubated with serial dilutions of soluble human recombinant TNF-α (□) and TNC-TNF [bacterial lysate (●)] at 37° C. for 16 h. The proportion of living cells was quantified by an MTT assay (see FIG. 1). The extinction was determined at 560 nm. The means±SD are depicted in each case.

3.2 Covalent Immobilization of TNF Fusion Proteins on Surface-Modified Carrier Particles The newly prepared TNF fusion proteins (see 3.1.1 and 3.1.2) were reacted with nanoparticles with a maleimido-activated surface (cf. Example 2.9) (final concentration of the nanoparticles between 500 and 1000 µg/ml).

The two coupling components were mixed and incubated in 2 ml of 10 mM sodium phosphate buffer pH 7.2 (final volume) at room temperature for 30-45 min. The particles were removed from the soluble component by centrifugation at 13 000 rpm (Eppendorf 5403 refrigerated centrifuge) at 4° C. for 10 min. The carrier-immobilized TNF fusion protein was washed twice with 1-2 ml of PBS and taken up in RPMI 1640 medium containing 5% FCS or PBS (depending on subsequent analyses).

3.3 Demonstration of the Immobilization and of the Biological Activity of Immobilized TNF It was demonstrated by means of bioassays and ELISA assays that the TNF molecules had been immobilized on the nanoparticles. The resulting nanoparticles with TNF immobilized thereon were characterized in relation to their biological activity by using defined cellular assay systems, in particular tumor cell lines. These cell systems enable sensitive detection of differential biological activity of soluble and nanoparticle-coupled TNF variants.

In particular, the cytotoxic effect on KYM-1 cells, Colo205 cells and MF-R2Fas cells (mouse fibroblasts with chimeric TNF receptor 2) of the nanoparticles of the invention with TNF immobilized thereon was determined. These cell systems enable sensitive detection of a differential bioactivity of soluble and matrix-coupled variants of TNF, as described in Grell et al., 1995, Grell et al., 1993, Krippner-Heidenreich et al., 2002. The effect of the nanoparticles of the invention with TNF immobilized thereon was compared with the effect of human recombinant TNF-α in solution as control. The assays for the effect of the nanoparticles of the invention and soluble TNF on the aforementioned cell lines took place by standard methods. These entailed the $EC_{50}$ values of immobilized TNF and TNF in solution being measured and compared.

Induction of apoptosis in TNF-sensitive tumor cell lines (see FIG. 4-7)

The KYM-1 cells for the bioassay were cultivated as described in FIG. 1.

The cells were incubated in the presence of titrated concentrations of the conjugates from coupling mixtures A 1-A 3 (cf. 2.1 for carriers) at 37° C. for 18 h. The proportion of living cells was determined by the MTT method. Human recombinant TNF-α (Δ) was employed as standard (see FIG. 1). The loading of the particles with CysHisTNF was determined by sandwich ELISA (OPTEIA™ Human TNF-α Elisa Kit, BD PharMingen).

Figure 4:
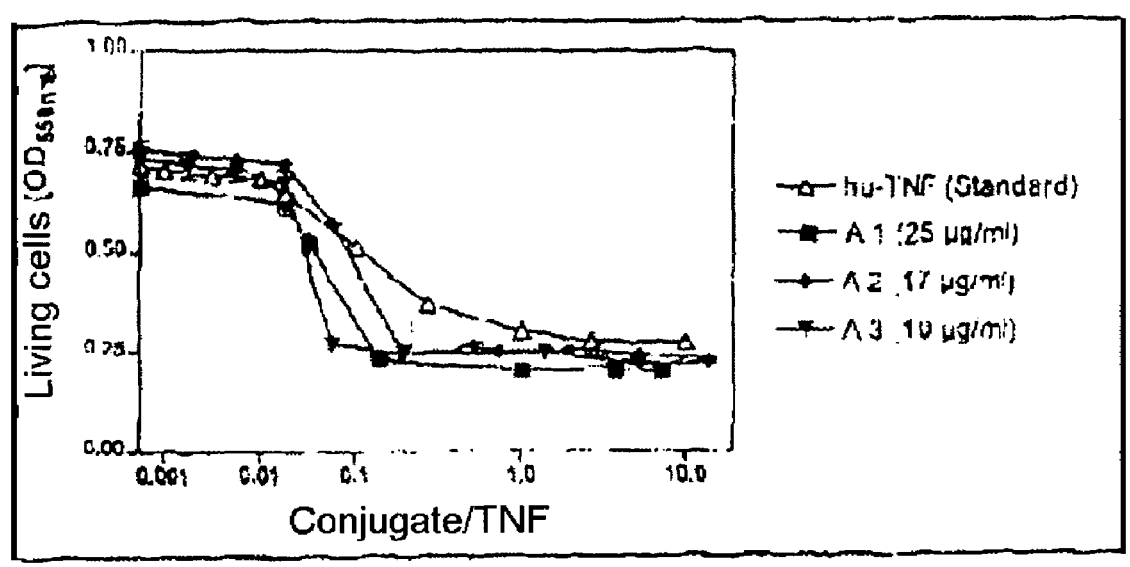
FIG. 4 shows the results of a bioassay where the effect of nanoparticles of the invention on KYM-1 tumor cells was investigated by comparison with that of soluble human recombinant TNF as control.
Figure 5:
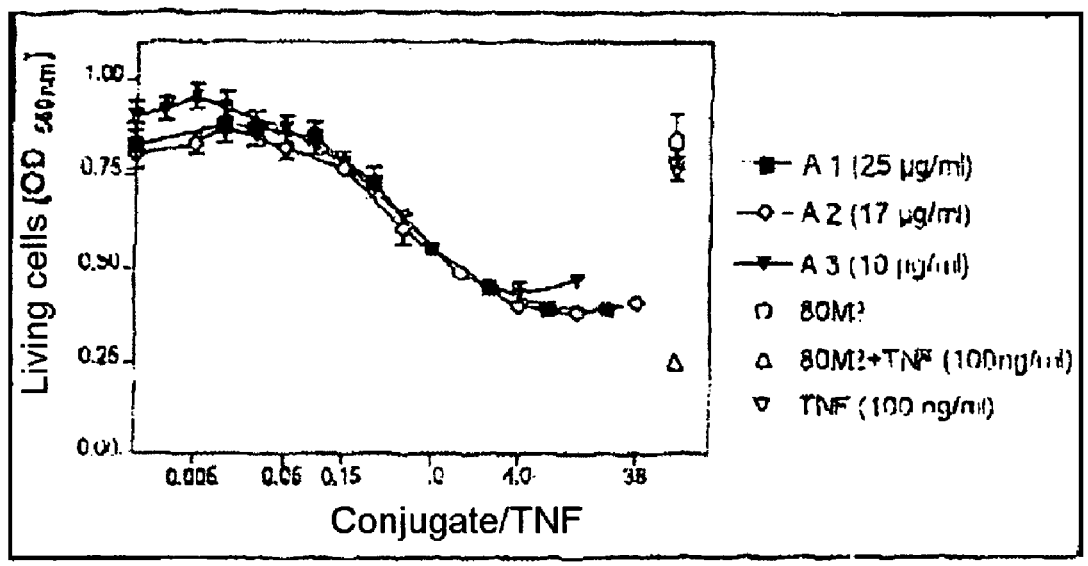
FIG. 5 shows the results of a bioassay where the effect of nanoparticles of the invention on Colo205 tumor cells was investigated by comparison with that of soluble human recombinant TNF as control. Controls were carried out with soluble human TNF with or without coincubation with the monoclonal antibody 80M2, which itself has no agonistic activity.

The results obtained using the KYM 1 tumor cell line are depicted in FIG. 4 and Table 1. Table 1 shows the $EC_{50}$ values for the TNF conjugates compared with human recombinant TNF-α.

TABLE 1

| Derivatives | $EC_{50}$ [ng/ml] | Range |
|---|---|---|
| Human recomb. TNF-α | 0.120 | 0.096-0.144 |
| Mixture A 1 ($c_0$ = 25 µg/ml) | 0.055 | 0.046-0.065 |
| Mixture A 2 ($c_0$ = 17 µg/ml) | 0.056 | 0.036-0.089 |
| Mixture A 3 ($c_0$ = 10 µg/ml) | 0.026 | 0.021-0.033 |

The bioassay to determine the effect of immobilized and non-immobilized TNF on the Colo205 target cells was carried out by standard methods. Control mixtures were in this case carried out with soluble TNF with or without coincubation with the monoclonal antibody 80M2 which itself has no agonistic activity. The results concerning the effect of the nanoparticles of the invention on these target cells compared with the effect of soluble human recombinant TNF on the Colo205 target cells are summarized in FIG. 5 and Table 2. For the bioassay, the colon carcinoma cell line Colo205 was seeded in 96-well microtiter plates ($1.1 \times 10^4$ cells/well) and incubated overnight as described in Grell et al., 1995. The Colo205 cells were incubated with serial dilutions of the conjugates from the coupling mixtures A 1-A 3 at 37° C. for 40 h. Colo205 cells were additionally cultivated with soluble human recombinant TNF-α (∇) in the absence and presence of the TNF receptor R2-specific antibody 80M2 (○, Δ; 1 µg/ml). This monoclonal antibody itself has no agonistic activity but, together with soluble hu-TNF, induces TNF receptor R2-specific signals (Grell et al., 1994). The proportion of living cells was determined by the standard MTT method (cf. FIG. 1). The loading of the particles with CysHisTNF was determined by sandwich ELISA (cf. FIG. 4).

TABLE 2

| Derivative | $EC_{50}$ [ng/ml] | Range |
|---|---|---|
| Mixture A 1 ($c_0$ = 25 µg/ml) | 0.64 | 0.44-0.93 |
| Mixture A 2 ($c_0$ = 17 µg/ml) | 0.45 | 0.33-0.61 |
| Mixture A 3 ($c_0$ = 10 µg/ml) | 0.28 | 0.185-0.411 |
| Human recomb. TNF-α | >100 | — |

The results of the biological assays carried out, and of the ELISA assays, prove that the TNF variants used were immobilized on the nanoparticles. The TNF molecules immobilized on the nanoparticles of the invention show, as is evident from FIG. 5, a bioactivity which is altered from that the soluble protein and resembles membrane-associated TNF. The Colo205 tumor cell line is substantially resistant to the cytotoxic effect of soluble TNF, whereas stimulation of the TNF-R2 receptor with membrane-associated TNF, the so-called pro-form of TNF, leads, just as with immobilized TNF, to the induction of apoptosis. The membrane TNF-equivalent properties of the TNF-conjugated nanoparticles (nanocytes) are confirmed in a further cell model in Example 4.

EXAMPLE 4

The following figures further prove the bioactivity on tumor cell lines which is mediated by conjugates/NANOCYTES. Surface-modified carriers having a dextran layer (CMD matrix, see 2.4) were employed in the examples described. Testing of the conjugates on suitable cells demonstrated the TNF receptor R2-stimulation via induction of apoptosis (see FIG. 6+7).

The specific biological activity/functionality of the conjugate was initially determined in a standardized cytotoxicity test on KYM-1 cells (for procedure, cf. FIG. 1 or 4). The carriers described in 2.4 were employed for the coupling mixture. Human recombinant TNF-α (□) was employed as standard. Unloaded particles have no apoptosis-inducing effect (◇). The proportion of living cells was determined by the standard MTT method. The loading of the particles with CysHisTNF (●) was quantified by sandwich ELISA.

Figure 6:
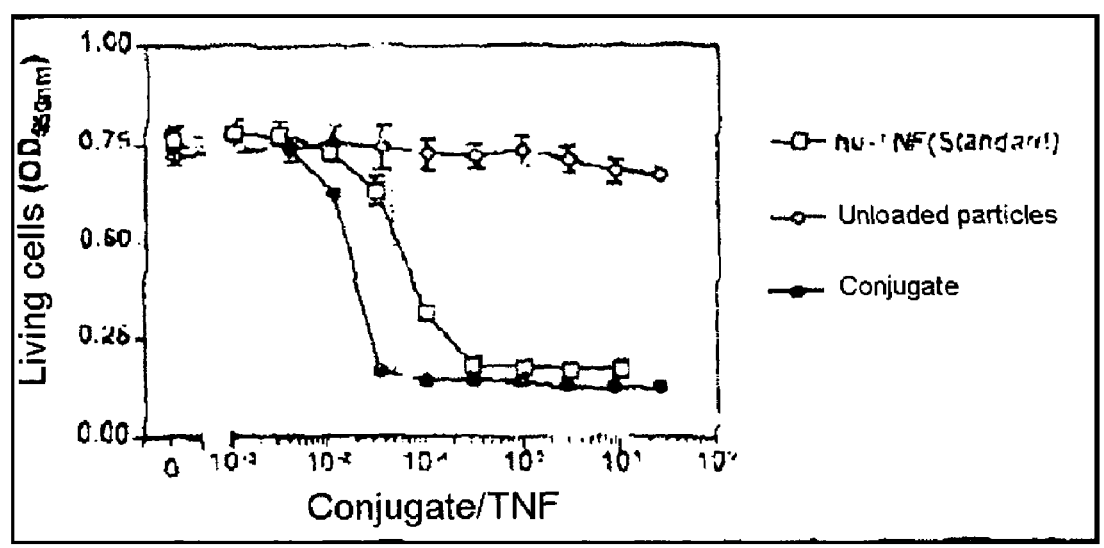
FIG. 6 shows the results of another bioassay with the KYM-1 target cell, where the effect of nanoparticles of the invention was investigated in comparison with the effect of soluble human recombinant TNF as positive control and nanoparticles not loaded with TNF as negative control.
Figure 7:
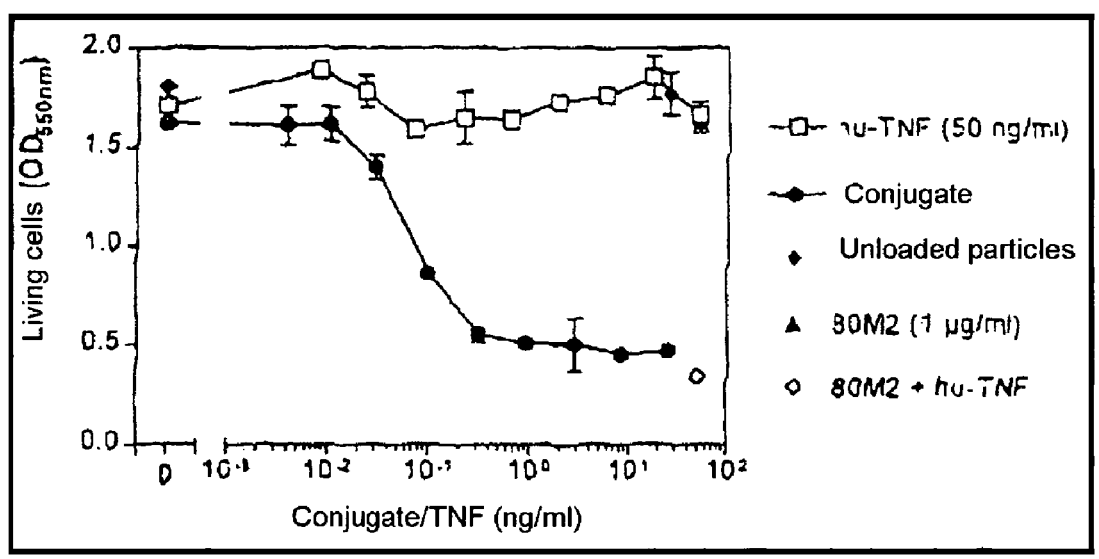
FIG. 7 shows the results of another bioassay with mouse fibroblasts which express human TNFR2 and thus are a cell model for detecting membrane TNF-like bioactivity. The figure shows the properties, comparable to the natural membrane TNF, of the TNF nanocytes (conjugate) compared with positive (80M2 plus TNF) and negative (hu-TNF, 80M2, unloaded particles) controls.

The biological activity of the conjugate described in FIG. 6 was determined in a further bioassay on mouse fibroblasts ($1.2 \times 10^4$ cells/well) (FIG. 7).

This cell line expresses a chimeric TNF receptor TNF-R2-Fas which comprises the cytoplasmic domain of the death receptor Fas (CD95) and the extracellular domain of the human TNF receptor R2, as described in Krippner-Heidenreich et al., 2002. The cell line is highly sensitive to the membrane form of hu-TNF-α [membrane-equivalent stimulus (◇), see FIG. 7], but substantially resistant to soluble hu-TNF-α (□). The proportion of living cells was determined by the crystal violet staining/method. The loading of the particles with CysHisTNF (●) was determined by sandwich ELISA (cf. FIG. 4).

It is thus shown that the matrix-coupled TNF has properties equivalent to membrane-associated TNF.

EXAMPLE 5

TNF and CysHisTNF interactions with TNF receptor 1 and TNF receptor 2

The following affinity measurements took place by means of waveguide spectroscopy resonance analyses using an IAsys instrument (Thermo-Labsystem Camebridge, Great Britain). In this case, modified tumor necrosis factor receptors 1 (TNFR1-Fc) or tumor necrosis factor receptors 2 (TNFR2-Fc) were immobilized via α-amino groups on a carboxymethyldextran matrix (CMD matrix). Binding studies were then carried out. For the binding, various concentrations of TNF or Cys-TNF on the receptors were followed online over time. Each binding was followed by a regeneration, e.g. the bound ligand was washed off the immobilized matrix. A receptor-loaded matrix was thus available for at least 10 bindings. It was then possible to determine the following parameters from the raw data obtained in this way:

1. Plotting the extent of binding of TNF for CysHisTNF (extent) against the concentration employed (ligate) results in a binding curve which, in the saturation region, describes the maximum possible binding (Bmax).

2. Plotting the ratio of the extent of binding and the TNF or CysHisTNF concentration (extent/ligate) against the extent of binding (extent) results in a line equation whose gradient corresponds to the negative affinity constant $K_D$ (Scatchard plot).

3. Plotting the association rate constant (con) against the TNF or CysHisTNF concentration is a further method for determining the $K_D$ and serves to determine the $K_D$ found in section 2. In addition, the intercept of the line with the Y axis corresponds to the half-life $t_{1/2}$ of the ligand-receptor complex and is thus a measure of the stability of the TNF- or CysHisTNF-receptor complex.

These three types of plots were chosen for CysHisTNF on immobilized TNFR1-Fc (FIG. 8), CysHisTNF on immobilized TNFR2-Fc (FIG. 9), TNF on immobilized TNFR2 (FIG. 10) and TNF on immobilized TNFR1-Fc (FIG. 11). At least two independent experiments were carried out in each case. As summarized in Table 4, it emerged that TNF and CysHisTNF bind with a similar affinity to the modified TNF-R1 receptor ($K_D$=2-5 nM). The half-lives of these ligands with TNFR1-Fc also correspond to one another, at 8 to 14 minutes. The latter is also the case for the half-lives on TNFR2-Fc, which are about 8 minutes for TNF and about 3 minutes for CysHisTNF. Only the affinity constants of TNF and CysHisTNF on modified TNFR2 are approximately an order of magnitude lower for CysHisTNF ($K_D$=10 nm for CysHisTNF and $K_D$=1 nM for TNF).

These values prove the high-affinity and specific binding of CysHisTNF to both known receptors. Although the numerical values were obtained with the aid of surface-coupled receptors (TNFR1-Fc and TNFR2-Fc) which were artificially dimerized, they nevertheless allow conclusions to be drawn about the receptor-binding situation of a cell where trimerization of the receptors takes place owing to the trimeric ligand.

The results are summarized in Table 4.

TABLE 4

| Ligand | Ligate | Matrix | $k_{on}$/ligate $K_{d\ average}$ [M] | $t_{1/2}$ [min] |
|---|---|---|---|---|
| TNF-R1-Fc | TNF | CMD | 6.8e−10 | 14.3 |
|  | TNF | CMD | 0.4e−10 | 99.3 |
|  | TNF | CMD | 17.0e−10 | 8.0 |
|  | mean |  | 3.61e−10 | 25.0 |
|  | CysTNF | CMD | 4.1e−10 | 22.4 |
|  | CysTNF | CMD | 7.0e−10 | 18.7 |
|  | mean |  | 5.57e−10 | 20.6 |
| TNF-R2-Fc | TNF | CMD | 1.24e−9 | 9.1 |
|  | TNF | CMD | 1.47e−9 | 7.3 |
|  | mean |  | 1.35e−09 | 8.1 |
|  | CysTNF | CMD | 4.06e−9 | 1.7 |
|  | CysTNF | CMD | 3.47e−9 | 4.2 |
|  | mean |  | 3.77e−09 | 2.4 |
| Cys-TNF | TNF-R1-Fc | AS | 5.8e−9 | 2.4 |
|  | TNF-R1-Fc | CMD | 27.8e−9 | 1.7 |
|  | TNF-R2-Fc | AS | 5.7e−9 | 8.1 |
|  | TNF-R2-Fc | CMD | 5.5e−9 | 3.0 |

REFERENCES

Grell, M., Krammer, P. H. and Scheurich, P. Segregation of APO-1/Fas antigen- and tumor necrosis factor receptor-mediated apoptosis. Eur. J. Immunol. 24, 2563-2566 (1994)

Grell et al., Cell 83, 793-802 (1995)

Grell et al., Lymphokine Cytokine Res. 12, 143-148 (1993)

Krippner-Heidenreich et al., submitted to J. Biol. Chem. (2002)

Meager, A. J. J. A cytotoxicity assay for tumor necrosis factor using a human rhabdomyosarcoma cell line. Immunol. Methods 144(1), 141-143 (1991)

Wüest, T. "Fibroblast activation protein" spezifische rekombinante Antikörperderivate zur Tumordetektion und Therapie. Dissertation University of Stuttgart, Shaker Verlag, Aachen (2001)

Wüest, T., Gerlach, E., Banerjee, D., Gerspach, J., Mossmayer, D., and Pfizenmaier, K. TNF-Selectokine: a novel prodrug generated for tumor targeting and site-specific activation of tumor necrosis factor. Oncogene 21, 4257-4265 (2002)

PCT Application WO 02/22833 (2002)

The invention claimed is:

1. A nanoparticle comprising a carrier with a surface having functional groups 1 A and at least three monomers of a protein of the TNF family (TNF: tumor necrosis factor), these at least three monomers having complementary functional groups 2 A, which bind functional groups 1 A and being connected via the functional groups 2 A to the functional groups 1 A of the carrier, where the three monomers are immobilized as a trimer on the nanoparticle, and where the protein of the TNF-family has a natural or synthetic multimerization module.

2. The nanoparticle as claimed in claim 1, where three monomers are each connected via their functional groups 2 A to the functional groups 1 A of the carrier.

3. The nanoparticle as claimed in claim 1, where at least one further monomer of a protein of the TNF family associated with the monomer connected to the carrier is immobilized on the nanoparticle.

4. The nanoparticle as claimed in claim 3, where two further monomers of one or more proteins of the TNF family associated with the monomer connected to the carrier are immobilized on the nanoparticle and thereby form a trimer.

5. The nanoparticle as claimed in claim 1, where the monomers are identical monomers.

6. The nanoparticle as claimed in claim 1, where the monomers are different monomers.

7. The nanoparticle as claimed in claim 1, where the protein of the TNF family is TNF-α, lymphotoxin LT-α, LT-β, FasL, TRAIL or CD40L.

8. The nanoparticle as claimed in claim 1, comprising a carrier with a surface having functional groups 1 A and, immobilized on the carrier, with at least one protein of the TNF family with complementary functional groups 2 A which bind the functional groups 1 A, where the protein of the TNF family is immobilized in the form of a trimer.

9. The nanoparticle as claimed claim 1, where the trimer, in particular TNF trimer, is immobilized on the carrier in directed fashion and with retention of its biological activity through covalent bonding between functional groups 1 A and 2 A.

10. The nanoparticle as claimed in claim 1, where the functional group 1 A is selected from the group consisting of amino group, carboxy group, epoxy group, maleimido group, alkyl ketone group, aldehyde group, hydrazine group, hydrazide group, thiol group and thioester group.

11. The nanoparticle as claimed in claim 1, where the complementary functional group 2 A which binds the functional group 1 A is selected from the group consisting of amino group, carboxy group, epoxy group, maleimido group, alkyl ketone group, aldehyde group, hydrazine group, hydrazide group, thiol group and thioester group.

12. The nanoparticle as claimed in claim 1, where the protein of the TNF cell is a synthetic, naturally occurring or recombinantly prepared protein with a wild-type sequence or with a mutated sequence.

13. The nanoparticle as claimed in claim 12, where the protein of the TNF family is in chemically modified form.

14. The nanoparticle as claimed in claim 1, where the protein of the TNF family has the tenascin C multimerization module.

15. The nanoparticle as claimed in claim 1, where the surface has further functional groups 1 B and the at least one monomer of the protein of the TNF family has further complementary functional groups 2 B which bind the functional groups 1 B.

16. The nanoparticle as claimed in claim 15, where a non-covalent binding is present between functional groups 1 B and 2 B.

17. The nanoparticle as claimed in claim 15, where the further functional group 1 B is selected from the group consisting of oligohistidine group, Strep tag I, Strep tag II, desthiobiotin, biotin, chitin, chitin derivatives, chitin binding domain, metal ion chelate complex, streptavidin, streptactin, avidin and neutravidin.

18. The nanoparticle as claimed in claim 15, where the complementary functional group 2 B which binds the functional group 1 B is selected from the group consisting of oligohistidine group, Strep tag I, Strep tag II, desthiobiotin, biotin, chitin, chitin derivatives, chitin binding domain, metal ion chelate complex, streptavidin, streptactin, avidin and neutravidin.

19. The nanoparticle as claimed in claim 1, where the functional group 1 A and/or 1 B is/are connected via spacers to the surface of the nanoparticle or is/are a constituent of a spacer.

20. The nanoparticle as claimed in claim 1, where the functional group 2 A and/or 2 B is/are connected via spacers to the at least one monomer of the protein of the TNF family or is/are a constituent of a spacer.

21. The nanoparticle as claimed in claim 1, where the functional group 2 A is a structural constituent of an unnatural amino acid of the at least one monomer of the protein of the TNF family, in particular of an amino acid derivatized with a spacer.

22. The nanoparticle as claimed in claim 1, where the functional group 2 A and/or 2 B is/are connected to a tethering group of the carrier.

23. The nanoparticle as claimed in claim 1, where the metal ion chelate complex comprises a divalent cation as metal component.

24. The nanoparticle as claimed in claim 23, where the metal ion chelate complex is an Ni-NTA (nickel-nitrilotriacetic acid) derivative.

25. The nanoparticle as claimed in claim 1, where the carrier consists of a biocompatible material.

26. The nanoparticle as claimed in claim 25, where the carrier comprises or consists of an inorganic material.

27. The nanoparticle as claimed in claim 26, where the inorganic carrier material is silicon, $SiO_2$, SiO, a silicate, $Al_2O_3$, $SiO_2 \cdot Al_2O_3$, $ZrO_2$, $Fe_2O_3$, $Ag_2O$, $Zr_2O_3$, $Ta_2O_5$, zeolite, $TiO_2$, glass, indium tin oxide, hydroxyapatite, Au, $Fe_3O_4$, ZnS, CdSe, calcium phosphate, calcium carbonate or a mixture thereof.

28. The nanoparticle as claimed in claim 25, where the carrier comprises or consists of an organic non-biodegradable material.

29. The nanoparticle as claimed in claim 28, where the carrier material is a polymer which is generated by free-radical polymerization.

30. The nanoparticle as claimed in claim 28, where the carrier material is polypropylene, polystyrene, a polyacrylate or a mixture thereof.

31. The nanoparticle as claimed in claim 25, where the carrier comprises or consists of a biodegradable material.

32. The nanoparticle as claimed in claim 31, where the carrier material is a polyester of polylactic acid, in particular poly(D,L-lactic acid-co-glycolic acid).

33. The nanoparticle as claimed in claim 32, where the polyester is additionally stabilized by crosslinking.

34. The nanoparticle as claimed in claim 1, where the carrier is compact or hollow and has a size of from 5 nm to 500 nm.

35. The nanoparticle as claimed in claim 1, where the carrier has additional functionalities.

36. The nanoparticle as claimed in claim 35, where the carrier has a fluorescent label, a UV/Vis label, a superparamagnetic function, a ferromagnetic function and/or a radioactive label.

37. The nanoparticle as claimed in claim 35, where the carrier has a chemical compound suitable for therapy and/or diagnosis.

38. The nanoparticle as claimed in claim 37, where the chemical compound is a cytostatic.

39. The nanoparticle as claimed in claim 35, where the carrier has a chemical compound which serves for steric stabilization and/or for preventing a conformational change of immobilized protein of the TNF family and/or for preventing the attachment of a further biologically active compound to the carrier.

40. The nanoparticle as claimed in claim 1, where the carrier has further biological functions, in particular ligands such as peptides or proteins, which are in particular tissue- or cell-specific.

41. The nanoparticles as claimed in claim 39 where the chemical compound is a polyethylene glycol, an oligoethylene glycol, dextran or a mixture thereof.

42. The nanoparticle as claimed in claim 1, where the immobilized protein of the TNF family has a marker.

43. The nanoparticle as claimed in claim 42, where the marker is a fluorophore, a spin label, a radioactive label and/or a gold particle, in particular attached to amino acids of the protein of the TNF family, preferably to its side chains.

44. The nanoparticle as claimed in claim 43, where the fluorophore is N-methylazatryptophan or a coumarin derivative such as DCA (6,7-dimethoxy-4-coumaryl) or NBD (N-β-7-nitrobenzofurazan-L-N-diaminopropionic acid).

45. The nanoparticle as claimed in claim 43, where the fluorophore is CyDye or Alexa.

46. A method for the directed immobilization of proteins of the TNF family on a nanoparticle with retention of their biological activity, where the surface of an inorganic or organic particulate carrier is modified by attachment of functional groups 1 A, and at least three monomers of a protein of the TNF family which have complementary functional groups 2 A are brought into contact with this surface in such a way that a covalent bonding between functional groups 1 A and 2 A takes place in such a way that the protein of the TNF family binds in a directed fashion and with retention of its biological activity to the nanoparticle.

47. The method as claimed in claim 46, where the functional groups 1 A and 2 A are selected from the group consisting of amino group, carboxy group, epoxy group, maleimideo group, alkyl ketone group, aldehyde group, hydrazine group, hydrazide group, thiol group and thioester group.

48. The method as claimed in claim 46, where molecules of the TNF family are immobilized as homo- or heterotrimers.

49. The method as claimed in claim 46, where the formation of the trimer takes place spontaneously.

50. The method as claimed in claim 46, where the formation of the trimer is brought about by a multimerization module contained in the molecule of the TNF family.

51. The method as claimed in claim 50, where the molecule of the TNF family comprises the tenascin C multimerization module.

52. The method as claimed in claim 46, where the surface of the carrier is modified by attaching further functional groups 1 B, and the molecules of the protein of the TNF family have further complementary functional groups 1 B, so that when the molecules are brought into contact with the surface a non-covalent binding between the functional groups 1 B and 2 B takes place.

53. The method as claimed in claim 52, where the functional groups 1 B and 2 B are selected from the group consisting of oligohistidine groups, Strep tag I, Strep tag II, desthiobiotin, biotin, chitin, chitin derivatives, chitin binding domain, metal ion chelate complex, streptavidin, streptactin, avidin and neutravidin.

54. The method as claimed in claim 46, where the functional groups 1 A, 1 B, 2 A and/or 2 B are connected with use of a spacer to the carrier and/or molecule of the protein of the TNF family or are a constituent of the spacer.

55. The method as claimed in claim 44, where the modification of the surface takes place by graft polymerization, silanization or chemical derivatization.

56. The method as claimed in claim 46, where the conditions under which the proteins are brought into contact with the surfaces are selected such that degradation of TNF is minimized or prevented.

57. The method as claimed in claim 46, where additional chemical compounds are attached for steric stabilization and/or to prevent a conformational change of the immobilized protein of the TNF family and/or to prevent the attachment of a further biologically active compound and/or with biological activity to the surface.

58. The method as claimed in claim 57, where the carrier has further biological functions, in particular ligands such as peptides or proteins, which are in particular tissue- or cell-specific.

59. The method as claimed in claim 46, where the nanoparticles are masked after immobilization of the monomer of the protein of the TNF family by use of a stealth method in order to achieve an adequate biocirculation.

60. The method as claimed in claim 59, where the nanoparticles are packaged in liposomes.

61. A method for identifying and/or detecting a substance which modifies, in particular promotes or inhibits, an interaction between immobilized protein of the TNF family and its complementary receptors, where a protein of the TNF family which is immobilized on a nanoparticle as claimed in any of claims 1, 2, 3-13 and 14-45 is incubated together with its receptors in the presence or absence of the substance to be tested, and an effect of the substance on the interaction between immobilized proteins of the TNF family and its receptors is detected.

62. The use of a nanoparticle as claimed in claim 1 for identifying and/or isolating a binding partner of immobilized protein of the TNF family.

63. The use of a nanoparticle as claimed in claim 1 for identifying and/or isolating inhibitors of the interaction of immobilized protein of the TNF family with its binding partners.

64. The use of a nanoparticle as claimed in claim 1 for preparing a pharmaceutical composition for the therapy of tumors, inflammatory disorders or disorders of the immune system, for wound healing or for modifying angiogenetic processes.

65. A pharmaceutical composition comprising a nanoparticle as claimed in claim 1.

66. A diagnostic composition comprising a nanoparticle as claimed in claim 1.

67. The method as claimed in claim 46, where the nanoparticles with TNF immobilized thereon are deposited on a membrane, and the film produced thereby is mechanically and/or chemically stabilized by crosslinking.

* * * * *

UNITED STATES PATENT AND TRADEMARK OFFICE
CERTIFICATE OF CORRECTION

PATENT NO. : 7,368,295 B2  Page 1 of 1
APPLICATION NO. : 10/488374
DATED : May 6, 2008
INVENTOR(S) : Gunter Tovar et al.

It is certified that error appears in the above-identified patent and that said Letters Patent is hereby corrected as shown below:

Title page, item

(73) Assignee should read:

Fraunhofer-Gesellschaft zur Förderung der angewandten Forschung e.V.

Signed and Sealed this

Twelfth Day of August, 2008

JON W. DUDAS
*Director of the United States Patent and Trademark Office*

SEQUENCE LISTING

<160> NUMBER OF SEQ ID NOS: 4

<210> SEQ ID NO 1
<211> LENGTH: 546
<212> TYPE: DNA
<213> ORGANISM: Homo sapiens

<400> SEQUENCE: 1

```
atgggagagc tcatcgaagg tcgctgcgcc ggtggatctg gtcatcatca tcaccatcac      60
ggctcagacg gagcgtcgtc ttcttctcgt accccgtctg acaaaccggt tgctcacgtt     120
gttgcaaacc cgcaggctga aggtcaactg caatggctga accgtcgtgc taacgctctg     180
ctggctaacg gtgttgaact gcgtgacaac cagctggttg ttccgtctga aggcctgtac     240
ctgatctact cccaggttct gttcaaaggc cagggctgcc cgttccaccca cgttctgctg     300
```

-continued

```
acccacacca tctctcgtat cgctgtttcc taccagacca aagtaaacct gctgtctgca    360
atcaaatctc cgtgccagcg tgaaacccg gaaggtgctg aagctaaacc gtggtacgaa    420
ccgatctacc tgggtggcgt ttttcaactg gagaaaggtg accgtctgtc tgcagaaatt    480
aaccgtccgg actacctgga cttcgcagaa tctggtcagg tttacttcgg tatcatcgct    540
ctgtga                                                               546
```

<210> SEQ ID NO 2
<211> LENGTH: 181
<212> TYPE: PRT
<213> ORGANISM: Homo sapiens

<400> SEQUENCE: 2

```
Met Gly Glu Leu Ile Glu Gly Arg Cys Ala Gly Gly Ser Gly His His
 1               5                  10                  15

His His His His Gly Ser Asp Gly Ala Ser Ser Ser Arg Thr Pro
            20                  25                  30

Ser Asp Lys Pro Val Ala His Val Val Ala Asn Pro Gln Ala Glu Gly
        35                  40                  45

Gln Leu Gln Trp Leu Asn Arg Arg Ala Asn Ala Leu Leu Ala Asn Gly
    50                  55                  60

Val Glu Leu Arg Asp Asn Gln Leu Val Val Pro Ser Glu Gly Leu Tyr
65                  70                  75                  80

Leu Ile Tyr Ser Gln Val Leu Phe Lys Gly Gln Gly Cys Pro Ser Thr
                85                  90                  95

His Val Leu Leu Thr His Thr Ile Ser Arg Ile Ala Val Ser Tyr Gln
            100                 105                 110

Thr Lys Val Asn Leu Leu Ser Ala Ile Lys Ser Pro Cys Gln Arg Glu
        115                 120                 125

Thr Pro Glu Gly Ala Glu Ala Lys Pro Trp Tyr Glu Pro Ile Tyr Leu
    130                 135                 140

Gly Gly Val Phe Gln Leu Glu Lys Gly Asp Arg Leu Ser Ala Glu Ile
145                 150                 155                 160

Asn Arg Pro Asp Tyr Leu Asp Phe Ala Glu Ser Gly Gln Val Tyr Phe
                165                 170                 175

Gly Ile Ile Ala Leu
            180
```

<210> SEQ ID NO 3
<211> LENGTH: 705
<212> TYPE: DNA
<213> ORGANISM: Homo sapiens

<400> SEQUENCE: 3

```
atgggaggat ccgtcgacct gcaggcctgt ggctgtgcgg ctgccccaga catcaaggac     60
ctgctgagca gactgaggga gctggagggg ctggtatcct ccctccggga gcagggtacc    120
ggaggtgggt ctggccccca gagggaagag ttccccaggg acctctctct aatcagccct    180
ctggcccagg cagtagccca tgttgtagca aaccctcaag ctgaggggca gctccagtgg    240
ctgaaccgcc gggccaatgc cctcctggcc aatggcgtgg agctgagaga taaccagctg    300
gtggtgccat cagagggcct gtacctcatc tactcccagg tcctcttcaa gggccaaggc    360
tgcccctcca cccatgtgct cctcacccac accatcagcc gcatcgccgt ctcctaccag    420
accaaggtca acctcctctc cgccatcaag agccctgcc agagggagac cccagagggg    480
gctgaggcca agccctggta tgagcccatc tatctgggag gggtcttcca gctggagaag    540
```

-continued

```
ggtgaccgac tcagcgctga gatcaatcgg cccgactatc tcgactttgc cgagtctggg      600
caggtctact ttgggatcat tgccctgtcc ggaatcgagg gtcgtggatc cgaacaaaag      660
ctgatctcag aagaagatct atcccatcat caccatcatc attaa                     705
```

<210> SEQ ID NO 4
<211> LENGTH: 234
<212> TYPE: PRT
<213> ORGANISM: Homo sapiens

<400> SEQUENCE: 4

```
Met Gly Gly Ser Val Asp Leu Gln Ala Cys Gly Cys Ala Ala Ala Pro
1               5                   10                  15

Asp Ile Lys Asp Leu Leu Ser Arg Leu Glu Glu Leu Glu Gly Leu Val
            20                  25                  30

Ser Ser Leu Arg Glu Gln Gly Thr Gly Gly Ser Gly Pro Gln Arg
        35                  40                  45

Glu Glu Phe Pro Arg Asp Leu Ser Leu Ile Ser Pro Leu Ala Gln Ala
    50                  55                  60

Val Ala His Val Val Ala Asn Pro Gln Ala Glu Gly Gln Leu Gln Trp
65                  70                  75                  80

Leu Asn Arg Arg Ala Asn Ala Leu Leu Ala Asn Gly Val Glu Leu Arg
                85                  90                  95

Asp Asn Gln Leu Val Val Pro Ser Glu Gly Leu Tyr Leu Ile Tyr Ser
            100                 105                 110

Gln Val Leu Phe Lys Gly Gln Gly Cys Pro Ser Thr His Val Leu Leu
        115                 120                 125

Thr His Thr Ile Ser Arg Ile Ala Val Ser Tyr Gln Thr Lys Val Asn
    130                 135                 140

Leu Leu Ser Ala Ile Lys Ser Pro Cys Gln Arg Glu Thr Pro Glu Gly
145                 150                 155                 160

Ala Glu Ala Lys Pro Trp Tyr Glu Pro Ile Tyr Leu Gly Gly Val Phe
                165                 170                 175

Gln Leu Glu Lys Gly Asp Arg Leu Ser Ala Glu Ile Asn Arg Pro Asp
            180                 185                 190

Tyr Leu Asp Phe Ala Glu Ser Gly Gln Val Tyr Phe Gly Ile Ile Ala
        195                 200                 205

Leu Ser Gly Ile Glu Gly Arg Gly Ser Glu Gln Lys Leu Ile Ser Glu
    210                 215                 220

Glu Asp Leu Ser His His His His His His
225                 230
```